United States Patent [19]
Mordehai et al.

[11] Patent Number: 5,352,892
[45] Date of Patent: Oct. 4, 1994

[54] ATMOSPHERIC PRESSURE ION INTERFACE FOR A MASS ANALYZER

[75] Inventors: Alex Mordehai; Gerard Hopfgartner, both of Ithaca; John D. Henion, Trumansburg, all of N.Y.

[73] Assignee: Cornell Research Foundation, Inc., Ithaca, N.Y.

[21] Appl. No.: 9,063

[22] Filed: Jan. 26, 1993

Related U.S. Application Data

[63] Continuation-in-part of Ser. No. 889,693, May 29, 1992, abandoned.

[51] Int. Cl.⁵ ................. B01D 59/44; H01J 49/00
[52] U.S. Cl. .............................. 250/288; 250/292
[58] Field of Search ............. 250/288, 281, 292, 288 A

[56] References Cited

U.S. PATENT DOCUMENTS

| | | | |
|---|---|---|---|
| 4,121,099 | 10/1978 | French et al. | 250/288 |
| 4,137,750 | 2/1979 | French et al. | 250/288 |
| 4,885,076 | 12/1989 | Smith | 250/288 |
| 4,948,962 | 8/1990 | Mitsui | 250/288 |

Primary Examiner—Bruce C. Anderson
Attorney, Agent, or Firm—Jones, Tullar & Cooper

[57] ABSTRACT

A novel atmospheric pressure ionization device for the transport of charged particle produced by at atmospheric pressure to a mass analyzer includes a liquid shield between the particle source and the sample inlet into the mass analyzer. The liquid shield may be in the form of a disk with a central aperture and acts as a spray splitter and aerofocusing device which increases the flow rate of a liquid sample into the analyzer. The mass analyzer is located in a high vacuum region and an intermediate low vacuum region is provided between the sample inlet and the analyzer. An ion optical system includes electrostatic lens assemblies in said vacuum regions for transporting charged particles from the inlet to the analyzer.

38 Claims, 13 Drawing Sheets

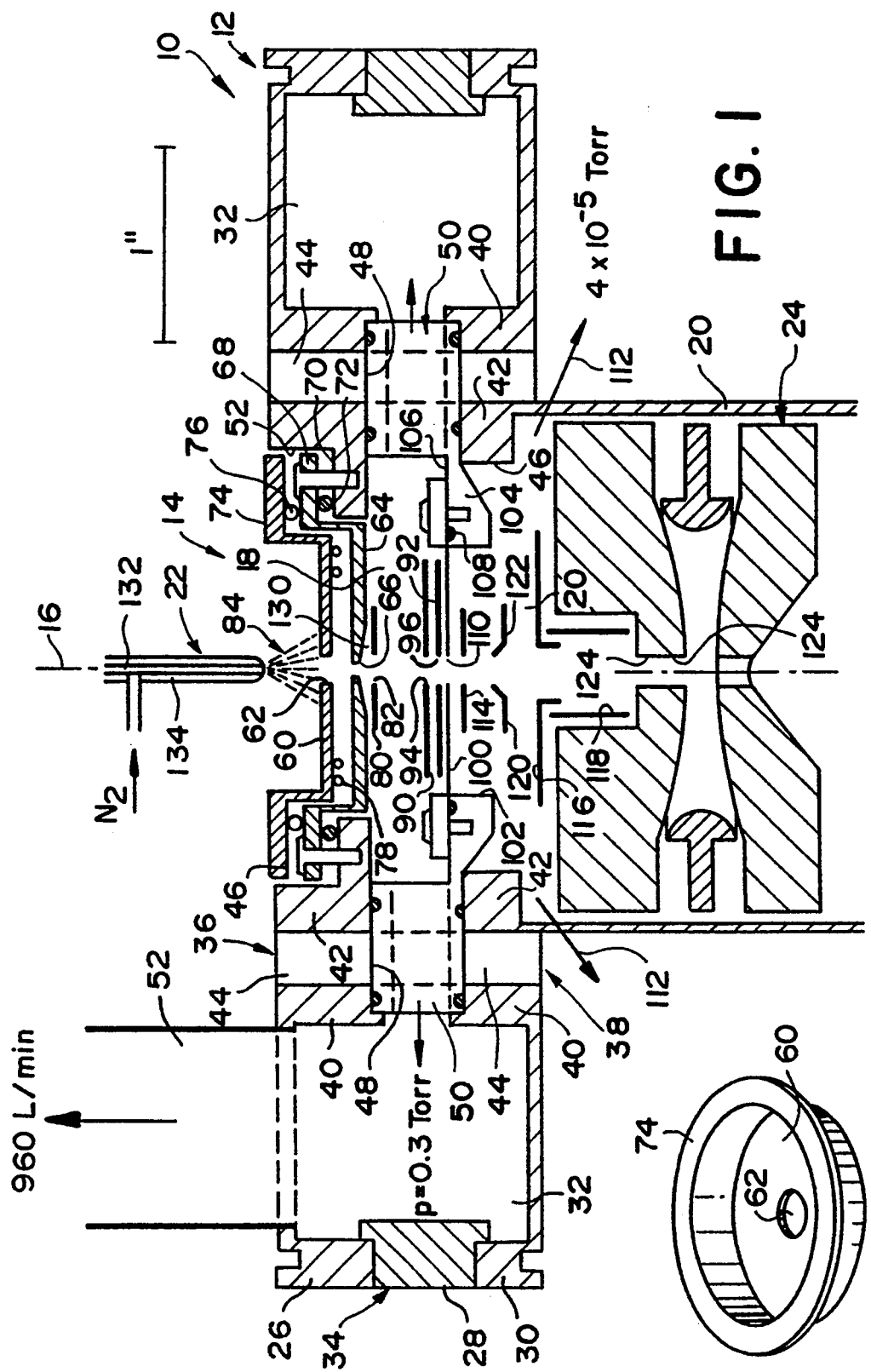

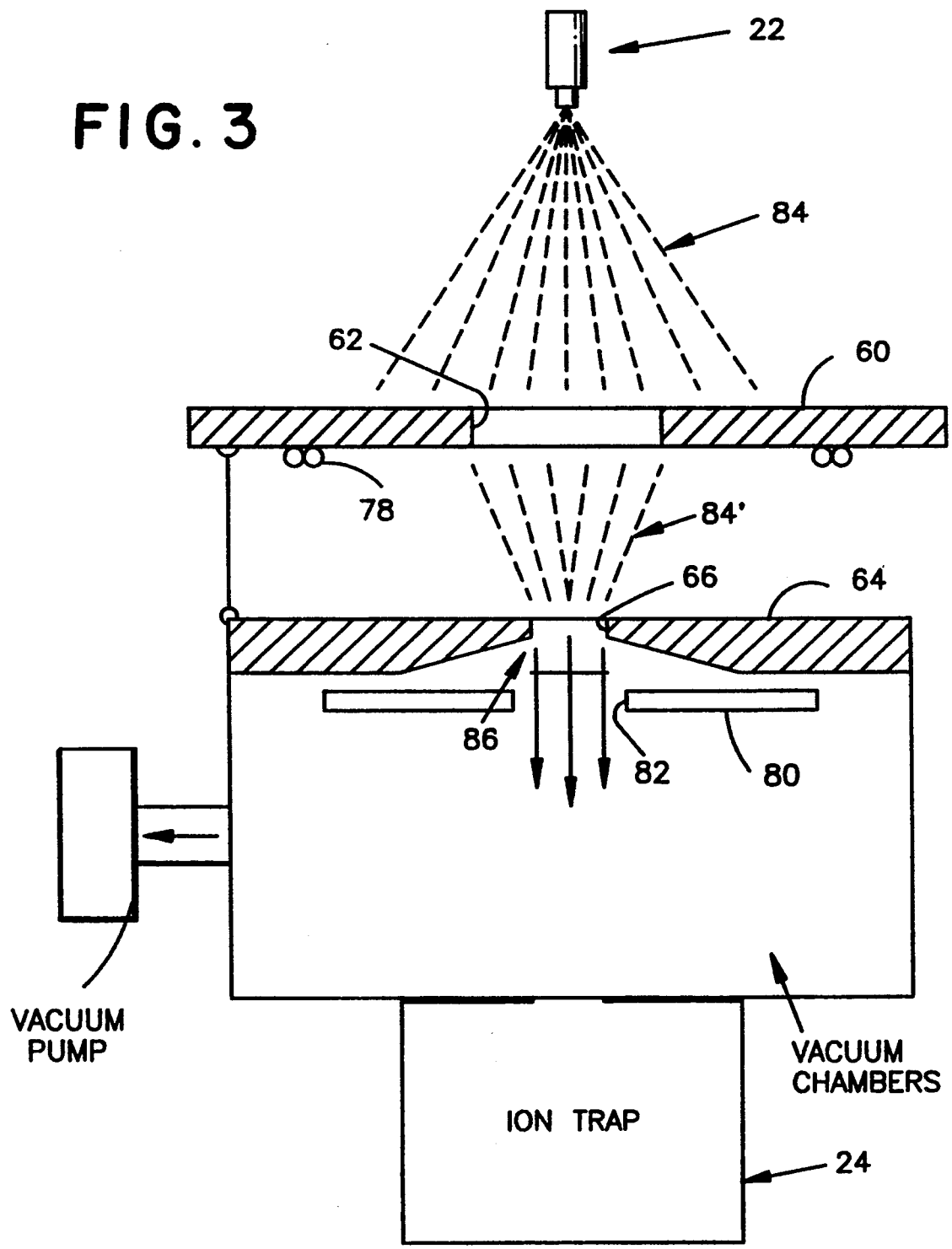

MASS SPECTRUM OF TETRABUTYLAMMONIUM HYDROXIDE

ATMOSPHERIC PRESSURE ION INTERFACE FOR A MASS ANALYZER

This application is a continuation-in-part of prior application Ser. No. 07/889,693, filed May, 29, 1992, now abandoned.

BACKGROUND OF THE INVENTION

The present invention relates, in general, to atmospheric pressure ionization techniques, and more particularly to an interface structure which utilizes atmospheric pressure ionization techniques such as electrospray, ion spray, and corona discharge ionization in combination with a mass analyzer.

The development of various spray techniques for forming ions from analytes was a significant advance in the field of mass spectrometry, for these techniques, and particularly those that employ electric fields to impart charges to droplets in the spray, permit the formation of highly charged ions (particles) from high molecular weight species. These highly charged ions are characterized by mass/charge ratios that are well within the range of values accessible to most modern mass analyzers.

In addition, the combination of mass analyzers with on-line separation methods, such as liquid chromatography, for mixtures in solution is becoming increasingly important. Mass spectrometry has long been recognized for its high sensitivity, but its use as a detector in combination with on-line separators of condensed-phase analytes has been limited at least in part because of the incompatibility of mass spectrometry to commonly used reversed-phase high-performance liquid chromatography (HPLC). The incompatibility arises, in part, from the use of a wide variety of buffer additives in the conventional HPLC eluent, high percentages of water in the eluent, and flow rates that are typically maintained at 1 mL/min., with standard 4.6 mm inner diameter HPLC columns. The HPLC eluent composition and its flow rate into the mass spectrometer have challenged the development of a routine and analytically rugged interface between the HPLC column and the mass spectrometer (LC/MS interface).

Historically, electron ionization (EI) mass spectra were produced from solutions introduced into a mass spectrometer at less than one microliter ($\mu$L) per minute. Later, chemical ionization (CI) mass spectra were generated by the introduction of aqueous solutions at 1-5 $\mu$L/min. into a CI mass spectrometer ion source. For this early work, the direct liquid introduction LC/MS interface was developed and commercially marketed through the early 1980's. This approach produced a modest beginning for LC/MS problem solving in several areas, but its limitation was the need for a 100-1 post column split, as described by J. D. Henion, "Drug Analysis by Continuously Monitored Liquid Chromatography/Mass Spectrometry with a Quadrupole Mass Spectrometer", Analytical Chemistry, 1978, No. 50, pp. 1687-1693, or the use of micro HPLC techniques, as described by Lee et al, Journal of Chromatography Science, 1986, No. 23, pp. 253-264. These were due to the vacuum pumping limitations imposed by conventional mass spectrometers. Thus, the liquid flow introduced into the CI ion source of these systems was limited to about 5 $\mu$L/min., and this limitation and the experimental difficulties associated with it discouraged many potentially interested researchers in the early days of LC/MS.

The introduction of thermospray LC/MS in the mid 1980's offered a significant breakthrough to the previous flow limitations discussed above. Thermospray LC/MS offered the realistic possibility of using conventional HPLC flows of 1.0-1.5 mL/min. with high aqueous eluent composition and volatile buffer additives such as ammonium acetate. The total HPLC effluent could be introduced into the mass spectrometer without the need for a post-column split or the use of micro HPLC techniques. Although the thermospray LC/MS approach offered an apparent simplification of the process in addition to providing three different modes of ionization, it was later learned that there could be a number of problems with the technique. These included widely varying response to different analytes, the need for different temperature settings for varying experimental conditions, thermal breakdown of some labile compounds, and the lack of structurally informative mass spectral information. Some of these needs were addressed with the introduction of particle beam LC/MS techniques which provided EI and CI mass spectra using HPLC flows in the neighborhood of 0.5 mL/min. However, this approach to LC/MS suffers from some limitations with regard to trace analyses and extends to involatile compounds of only slightly higher molecular weight, than can be handled by capillary gas chromatography/mass spectrometry (GC/MS).

Recently, considerable interest has developed in electrospray ionization as a new means of handling intractable, higher molecular weight compounds. Following initial results that demonstrated very good sensitivity for polar and high molecular weight compounds, interest has developed in combining HPLC with electrospray mass spectrometry. Unfortunately, however, electrospray returned the art to the very slow HPLC flow rates originally produced by the direct liquid introduction LC/MS interface described above. In particular, pure electrospray currently is limited to effluent flows of 1-5 $\mu$L/min. More recently with implementation pneumatically assisted electrospray [A. P. Bruins et al, Anal. Chem., v.59, p.2642(1987)] higher flow (up to 50 $\mu$L rates) became routine in practice of HPLC- mass spectrometry. However, at higher flow rate significant chemical noise causes problems: more solvated ions entering the mass spectrometer thus resulting in more noisy mass spectra as well as micro droplets produced by the spray at higher flow rates tend to plug the ion sampling orifice and produce random "spikes" in the chromatographic profile. This behavior is not acceptable, and it is preferred to use conventional HPLC flows of 1-1.5 mL/min. without any additional experimental constraints, while still obtaining low nanogram or better detection limits.

SUMMARY OF THE INVENTION

It is, therefore, an object of the present invention to provide an improved sampling device for mass analyzers which will maintain the good sensitivity and low chemical noise of the analyzer while permitting high flow rates for the supplied liquid analyte.

More particularly, it is an object of the present invention to provide an ion sampling device for coupling the delivery of an analyte carried by a liquid flow to a mass analyzer such as a quadrupole ion trap for on-line chromatography mass spectrometry.

Still more particularly, it is an object of the invention to provide an ion sampling device for coupling the delivery of an analyte carried by a liquid flow to a mass analyzer such as a quadrupole mass analyzer for on-line chromatography-mass spectrometry.

A still further object of the invention is to provide an interface between a liquid sample separator device such as a high performance liquid chromatographic column and a mass analyzer such as a quadrupole ion trap mass analyzer, a magnetic sector mass spectrometer, a time of flight mass spectrometer, a Fourier Transform mass spectrometer, or any like mass analyzer device.

Another object of the invention is to provide an ion sampling device for introducing liquid analyte into a mass analyzer at a rate which permits operation of a liquid chromatography system at high efficiency, while simplifying the analysis and increasing the sensitivity of the analyzer.

The principle limitation of atmospheric pressure spraying techniques in the production of ions for a mass analyzer is the liquid flow rate of the analyte. In pneumatically-assisted electrospray or ion spray, a flow rate of up to 1 milliliter per minute of is able to produce a charged spray of liquid droplets with reasonable analyte ion response. However, because of current limitations in the ion sampling devices for API/MS, applications can only handle flows of about 50 microliters per minute. Standard HPLC applications require splitting of the eluent before it is sprayed, and this hampers qualitative and quantitative analysis. At the milliliter/min. flow rates, unless there is post-column splitting, the excess HPLC effluent condenses at the interface and adversely affects sensitivity and ion current stability.

In accordance with the present invention, the problem of excess eluent at the inlet to a mass analyzer is avoided by placing a liquid shield lens in the open atmospheric pressure region, approximately 1-5 millimeters from the ion sampling inlet of the analyzer. The liquid shield lens acts as a spray splitter and an aerofocusing device and serves to inhibit collapsing droplets from being drawn to the interface and from generating unstable ion current. This results in an increased liquid flow to the analyzer and provides increased sensitivity and ion current stability in the mass analyzer. The region between the liquid shield lens and a sample inlet orifice for the analyzer preferably is heated to facilitate the droplet evaporation which is required for rapid ion evaporation from the charged liquid droplets. To create efficient transport of gas phase ions towards the ion sample inlet orifice, the analyte is aerodynamically accelerated by a carrier gas toward the liquid shield lens.

The liquid shield lens preferably is in the form of a thin, flat metal disc or plate having a circular aperture axially aligned with the sample inlet orifice. Alternatively, the shield may be "hat-shaped"; i.e., formed as a flat disc with a raised central circular mesa in which the aperture is located, the mesa surrounding the aperture and being axially aligned therewith. The upper surface of the mesa, in which the aperture is located, is spaced above the surrounding disc by about 4 mm, with the disc itself being spaced approximately 1 mm above the sample inlet orifice.

The liquid shield of the present invention may be used with a variety of mass analyzers, and revolutionizes the electrostatic ion spray process with a mass spectrometer by eliminating the problem of slow flow rates. This allows direct coupling of modern liquid separation technologies (HPLC, etc.) with mass spectrometry for on-line analysis.

The liquid shield lens of the present invention may be used with a variety of mass analyzers and different types of ion sampling inlets to protect the inlet sampling orifice of the vacuum portion of the system. For purposes of illustration, the present invention will first be described in combination with an ion trap mass spectrometer which includes an ion sampling inlet as a nozzle; a vacuum housing with a vacuum source for production of vacuum therein; an electrostatic lens system situated in the vacuum housing; a flat diaphragm separating a first vacuum region in the housing from a second, mass analyzer vacuum region, and an ion optical system for ion focusing and injection into, for example, an ion trap mass analyzer. Ions pass into the vacuum housing through the inlet nozzle, which separates ambient atmospheric pressure from the first, or interface, vacuum region in the housing. These ions experience extensive cooling in the supersonic jet which is the result of directional air expansion from the nozzle. At a location in the housing remote from the nozzle outlet, the excess gas is pumped away by the vacuum and gas molecules move in random motion in this low-vacuum region. A focusing electrostatic lens assembly directs the ions through this region and through a Mach disc to the mass analyzer vacuum system. It has been found that incorporating focusing ion optics in the first, or interface, vacuum region with the first lens electrode situated in the ion flow path prior to the Mach disc region, provides at least a 5-fold increase in the efficiency of the ion transport, while the provision of the liquid shield lens of the present invention with preheating of spray droplets at atmospheric pressure provides an approximately 4-fold increase in sensitivity.

Ions from the interface vacuum region pass into the mass analyzer vacuum region through an aperture in a flat diaphragm which divides the two regions and which also serves as an electrostatic lens. The mass analyzer vacuum region includes additional ion optics which consist of a second electrostatic lens assembly and pulsed ion beam deflector electrodes which direct the ions into a conventional ion trap.

The liquid shield may also be incorporated in other atmospheric pressure ionization systems with quadrupole mass analyzers to provide a breakthrough in routine analysis that can be carried out with conventional HPLC flow rates. For purposes of illustration the ion sampling device is also described with a set up for a quadrupole mass analyzer and different arrangements for a two stage mass analyzing vacuum system. Such an LC/MS system provides mass spectra for low nanogram quantities of environmentally and pharmaceutically important compounds injected on-column, using either volatile or non-volatile buffer additives.

BRIEF DESCRIPTION OF THE DRAWINGS

The foregoing, and additional objects, features and advantages of the present invention will become apparent to those of skill in the art from the following detailed description of a preferred embodiment thereof, taken in conjunction with the accompanying drawings, in which:

FIG. 1 is a diagrammatic illustration, in cross-section, of an atmospheric pressure ionization ion sampling device for an ion trap mass analyzer, utilizing the liquid lens shield of the present invention;

FIG. 2 is a perspective, diagrammatic view of the liquid lens shield of FIG. 1;

FIG. 3 is an enlarged diagrammatic illustration of the liquid shield lens portion of the apparatus of FIG. 1;

DESCRIPTION OF PREFERRED EMBODIMENTS

Figure 4:
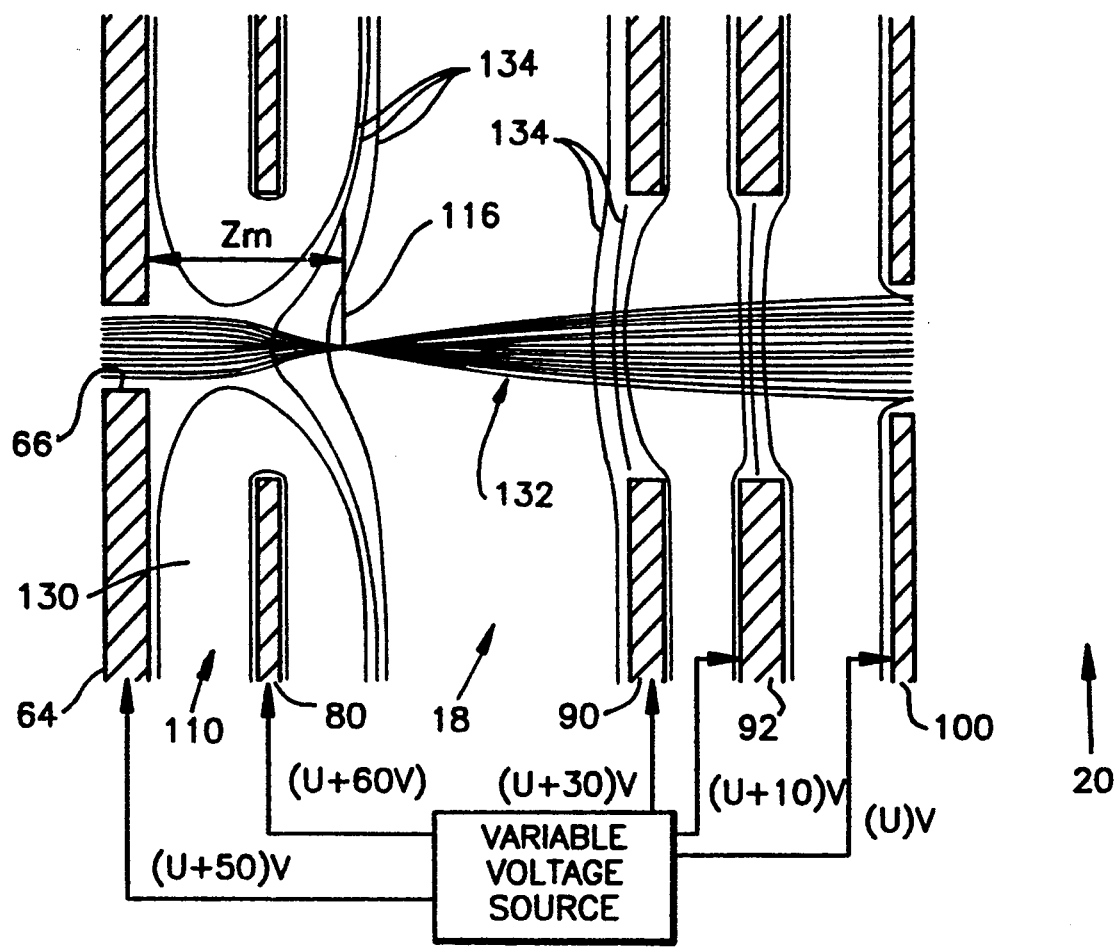
FIG. 4 is a plot of the electrostatic field and ion trajectories in a first vacuum region of the apparatus of FIG. 1.

Turning now to a more detailed consideration of the invention, there is illustrated in FIG. 1 a diagrammatic cross sectional view of an atmospheric pressure ionization (API) ion trap interface, generally indicated at 10, which connects a source of analyte liquid to a mass analyzer, here illustrated as an ion trap mass spectrometer, for the purpose of determining the mass spectrum of the analyte. In the illustrated embodiment, the interface 10 includes a housing 12 which is generally annular in shape and which has a central opening 14 having an axis 16. Within the central opening 14 is an interface stage, or chamber 18 and a mass analyzer one-stage vacuum system or chamber 20. The vacuum chambers 18 and 20 are axially aligned with each other along the central axis 16 of the interface. The upper surface (as viewed in FIG. 1) of the interface 10 receives ions produced from an analyte liquid by an electrospray apparatus diagrammatically illustrated at 22 and the interface directs the ions to a conventional ion trap mass analyzer 24 such as a benchtop Saturn II Ion Trap Detector from Varian Instruments, Palo Alto, Calif.

The interface housing 12 includes an annular top wall 26, a cylindrical flange 28 and an annular bottom wall 30 which are assembled and cooperate to define an outer annular pumping chamber or cavity 32. The flange 28 cooperates with corresponding outer edges of top and bottom walls 26 and 30, respectively, to form a cylindrical outer wall 34 for chamber 32, while inner edges of the annular top and bottom walls 26 and 30 are shaped to form upper and lower double walls 36 and 38, respectively, which cooperate to form inner and outer cylindrical walls 40 and 42. Wall 40 forms the inner wall of chamber 32, and walls 40 and 42 are radially spaced to define an inner annular chamber 44 therebetween. Wall 42 defines an inner annular surface 46 which surrounds and defines the central opening 14 for the housing 12. The central opening 14 receives interface nozzle and lens assemblies to be described, encloses the low chamber 18, and leads to vacuum chamber 20.

Secured within the inner annular surface 46 formed by the top and bottom walls 26 and 30 is an annular ion trap mounting flange 48 which secures the interface 10 to the ion trap 24. The mounting flange 48 includes a plurality of radial holes 50; for example, eight holes, spaced symmetrically around and extending through the annular walls 42 and 40, the holes extending radially between the vacuum chamber 18 and the pumping chamber 32. An outlet port 52 in the top wall 26 connects the pumping chamber 32 to a standard rotary vacuum pump (not shown), such as pump model D-60A available from Leybold, Inc., Export, Pa., which is capable of pumping 960 L per minute to produce a pressure of 0.3 Torr in chamber 32. The radial holes 50 may be 0.5 inch in diameter and the distribution of the holes around the circumference of inner surface 46 provides efficient and homogeneous pumping of the vacuum chamber 18.

The interface 10 includes a liquid shield lens 60 illustrated diagrammatically in FIG. 1 and in top perspective view in FIG. 2, the shield having a central aperture 62 coaxial with the axis 16 of the interface. The liquid shield 60 is mounted upstream of a sampling nozzle plate 64 at the interface inlet, the nozzle plate having a central aperture 66 coaxial with aperture 62 and with the central axis 16 of the interface. Nozzle plate aperture 66 may be, for example, 75 micrometers in diameter and may have a thickness of 225 micrometers to provide an aspect ratio of ⅓ (i.e., 75 micrometers/225 micrometers). The nozzle plate 64 includes an outwardly extending flange 68 extending over and mounted on an inwardly extending shoulder 70 formed on the annular surface 46 of wall 42 and is sealed thereto by means of a gasket or O-ring 72. Similarly, the liquid shield 60 includes an outwardly-extending flange 74 which is sealingly mounted on nozzle plate 64 by means of a suitable gasket or O-ring 76 to close the top of the vacuum chamber 14 and to insure that inlet flow is through apertures 62 and 66. Although only a single shield 60 is shown, it will be understood that multiple spaced, parallel shields with coaxial apertures may be used.

Located between the liquid shield lens 60 and the nozzle plate 64 is a heater element 78 which provides a heated atmospheric pressure region at the interface entrance.

Coaxial with apertures .62 and 66 and aligned below nozzle plate 64 is a first electrostatic lens assembly located in low-vacuum region 18 and including a first lens, diagrammatically illustrated at 80 having a central aperture 82. Ions, such as those diagrammatically illustrated at 84, are produced from the analyte liquid in conventional manner by electrospray apparatus 22 and are directed axially toward the interface 10 and enter the interface by way of aperture 62 in the liquid shield lens 60.

FIG. 3 illustrates in an enlarged view the relationship between the electrospray apparatus 22, the liquid shield 60, and the nozzle plate 64. As will be more fully described below, the spray apparatus 22 provides a spray 84 of charged droplets, ions and/or particles, which will be referred to herein as ions, at atmospheric pressure which are aerodynamically accelerated and directed toward the interface liquid shield 60. A portion of the spray strikes the upper surface of the shield 60, but a sample portion passes through the aperture 62 at atmospheric pressure and travels toward the sampling nozzle 66, as indicated by ion spray sample 84'. The liquid shield 60 is situated in a "soaking" region of the sampling nozzle 66; i.e., is spaced between 0.1 mm and 5 mm from the nozzle and is concentric with it. The liquid shield effectively protects the sampling nozzle from being plugged or restricted by liquid droplets from the spray 84, thereby significantly increasing the efficiency of ion sampling and allowing operation at a higher flow rate of liquid from the spray apparatus 22. As indicated diagrammatically by the pattern of ions at 84', the liquid shield provides an aerodynamic focusing of ions toward the aperture 66 of sampling nozzle 64, thereby enhancing the flow of ions into the ion sampling device. The heater 78 enhances this flow by alleviation ion formation from charges spray microdroplets in the region between the liquid shield and the nozzle plates.

The sample ions 84' are drawn through the nozzle aperture 66 by the vacuum in the interface vacuum chambers 18 and 20 and expand at the nozzle exit 86 to form a supersonic ion jet as they enter the first low vacuum region of chamber 18 and pass through aperture 82 of lens 80. The ions travel across the vacuum region 18 to the high vacuum chamber 20 through second and third electrostatic lenses 90 and 92 (FIG. 1) having central apertures 94 and 96, respectively, which are coaxial with the interface axis 16. Collision-induced dissociation (CID) processes may be induced in the ions in the first vacuum region 18 by imposing a potential difference between the nozzle plate 64 and a diaphragm 100 (FIG. 1) which divides the two chambers 18 and 20.

Diaphragm 100 extends across a central aperture 102 formed in the ion trap mounting flange 48. For this purpose, flange 48 includes an annular shoulder portion 104 which extends inwardly into the central opening 14 of housing 12. This shoulder portion has a top surface 106 to which the diaphragm 100 is secured and sealed by means of a suitable O-ring or gasket 108. The diaphragm 100 includes a central orifice 110 which is coaxial with the axis 16 of the interface, the orifice having a diameter of about 400 micrometers, in one embodiment.

The lower vacuum chamber 20 is connected to a standard 60 L per second turbomolecular pump, which may be a Model TPU-60 furnished by Balzers, Inc. of Hudson, N.H., for example (not shown) that is furnished as a standard part of the Saturn II ion trap detector. This pump produces a pressure typically in the range of $4 \times 10^{-5}$ Torr in the high vacuum region 20 and in the region of the ion trap 24, as indicated by arrows 112 in FIG. 1.

In the high vacuum region below diaphragm 100 is a second electrostatic lens assembly including lenses 114, 116 and 118 all having central apertures coaxial with axis 16 of the interface. Interposed between the lenses 114 and 116 are pulsed ion beam deflector electrodes 120 and 122. Coaxially aligned below the electrostatic lens 118 is the ion trap inlet aperture 124 leading to the ion trap device 24.

In the embodiment of FIG. 1, some of the ions 84 produced under atmospheric pressure conditions pass through aperture 62 in the heated, atmospheric pressure liquid shield lens 60. These selected ions 84' (FIG. 3) then pass through the aperture 66 in nozzle plate 64 into the first vacuum region 18. The ions next pass through the first electrostatic lens assembly, which includes lens electrodes 80, 90 and 92, into the mass analyzer vacuum region 20 through the 400 micrometer diameter orifice 110 in the diaphragm 100. Under operational conditions, the pressure in the first vacuum region 18 is 0.3 Torr, as noted above, while the pressure in the high vacuum region 20 is typically $4 \times 10^{-5}$ Torr. During operation of the device, helium damping gas is introduced into the high vacuum region to produce a total pressure in that region of $2 \times 10^{-4}$ Torr. The ions passing through the diaphragm orifice 110 then pass through the second electrostatic lens assembly, which includes lens elements 114, 116 and 118 and through deflector electrodes 120 and 122 in the high vacuum chamber and are supplied to the ion trap 24 by way of aperture 124. The ion trap, is housed in its original vacuum chamber within the Saturn II system.

The electrical potentials on nozzle plate 64, the separating diaphragm 100, and the ion optics electrodes are controlled by eight independent voltages taken from a single 130 volt DC power supply, these voltages being connected to the electrodes in known manner. The atmospheric pressure liquid shield lens 60 is maintained at the same potential as the nozzle plate 64. Further, the electric heater 78 is connected to the power supply through a suitable controller to maintain the temperature at the nozzle plate at, for example 250° C. The deflector electrodes 120 and 122 are controlled by a suitable transistor-transistor-logic (TTL) pulses produced by the electronic control board in the Saturn II system (not shown). The deflection voltage on these electrodes is controlled between 0 and 100 volts to control the path of the ion beam from the nozzle 64 to ion trap aperture 124, the control signal allowing ions to flow into the ion trap for a predetermined period of time (for example, 0.25 sec.), and thereafter deflecting the beam from the entrance of the ion trap to permit MS detection.

Optimization of any ion optic system depends upon the concepts of ion transport theory. Some of the most important aspects involve the fundamentals of beam emittance and phase-space acceptance of the analyzer. The term beam emittance refers to the area occupied by ions in a beam produced from an ion source. The phase-space is generally defined by the six-dimensional space which includes the ion coordinates (x, y, z) and their corresponding velocities ($V_x$, $V_y$, $V_z$). Since the velocities of the particles are directly related to their kinetic energy, energy can be substituted for velocity to define phase space (x, y, z, $E_x$, $E_y$, $E_z$) where $E_x$, $E_y$, $E_z$ are the kinetic energies of the ions in the corresponding directions. Ion acceptance by the mass analyzer is the phase space area representing all possible combinations of coordinates and velocities of the ions which can be successfully transmitted and detected in a mass analyzer. It can be shown that maximum transmission of any ion optical system is achieved when a transformation of the ion emittance in the phase space matches the acceptance. The usefulness of these concepts is a consequence of Liouvilles' theorem which states that as long as the ions in the beam are acted upon only by conservative forces (an electrostatic focusing field, for example) the area occupied by the ions remains constant. Furthermore, the action of many simple ion optical elements can be described as a simple mathematical linear transformation into phase space while a complex system can be segmented and treated individually.

The total ion optical system of the ion trap embodiment illustrated in FIG. 1 may be considered as two separate ion optical systems: the ion optics of the first, or interface, vacuum region 18 and the ion optics of the second, or mass-analyzing region which includes the high-vacuum region 20 and the ion trap 24. In the first vacuum region aerodynamic forces have a significant impact on ion motion and, accordingly, concepts of ion transport theory cannot be applied without several assumptions. In the second vacuum region, ion transport theory is directly applicable.

The confinement properties of an ion trap for capturing externally produced ions has been analyzed, but there is no mathematical expression for the acceptance of externally produced ions. However, this can be calculated using a simple model of collisional relaxation. In this model it is assumed that some mechanism for the dissipation of ion kinetic energy from the external beam exists in the trap to achieve confinement. The most effective way to obtain energy dissipation is through the scattering of ions by the damping gas (collisional relaxation). The criteria for ion trapping in this case is the loss of kinetic energy during passage through the trap, so its total energy will be less than the depth of the pseudopotential well D, produced by the RF potential of the trap:

$$E_2 < \frac{eA^2}{4m (z_0)^2 \omega^2} = D \text{ (SGS system of units)} \qquad (1)$$

where A is amplitude, $\omega$ is angular frequency of the RF potential, e/m is the charge to mass ratio of the ion and $z_0$ is the axial dimension of the ion trap.

Since the mass of the damping gas particle (usually He) is much lower than the mass of ions of interest, the following equation for the energy of ions to be captured by the trap (loss of kinetic energy $<<$ than initial kinetic energy) can be approximated:

$$E_1 = D \qquad (2)$$

where $E_1$ is the primary energy of the ion beam before collision. Using typical values during ion formation in the Saturn II system, $A=260$ $V_{0-p}$ (150 DAC), $\omega=3.3$ MHz, $z_0=1$ cm and m=300 amu, the value of D would be 20 eV.

After analyzing the acceptance properties of the ion trap 24 it can be concluded that the acceptance of the ion trap represents a limited area in the phase space ($d_i$, D) where $d_i$ represents dimensions of the ion trap entrance aperture 124 and D represents the limitation of the ion kinetic energy.

The probability of confinement of externally produced ions in this model equals the probability Z of a one-ion collision with a damping gas particle during passage through the ion trap:

$$Z = 2sn_0P_1z_0 \qquad (3)$$

where s is the collisional cross section, $n_0$ is density number at atmospheric pressure ($2.7 \times 10^{19}$ $cm^{-3}atm^{-1}$) and $P_1$ is the pressure in the mass analyzing region (in [atm]).

Equation 3 predicts that there is a linear relationship between the probability of ion confinement and the pressure of the damping gas. Under typical operational conditions $P_1 = 1$ mTorr ($1.2 \times 10^{-4}$ Torr Bayard-Alpert ionization gauge); $s = (1-2) \times 10^{-15}$ $cm^2$ ("small" ions) and $z_0 = 1$ cm; and the trapping efficiency is 7–15%. However, in practice, the actual trapping efficiency will be lower than the theoretical value because a fraction of the ions (those with higher kinetic energy) during the trapping period (prior to detection) will be lost. In addition, the ion trapping volume is always smaller than the geometric volume of the trap so the actual path length yielding ion confinement is smaller than $2z_0$, the geometric distance between the end cap electrodes, used in Eq. 3.

In the atmospheric pressure ionization (API) technique of the embodiment of FIG. 1, ions 84 are produced at atmospheric pressure by an API source 22 outside the vacuum chamber. These ions are introduced to the mass spectrometer 24 through a nozzle (or capillary), such as nozzle aperture 66, and are directed into the mass spectrometer. The properties of this API ion source 22 are significantly different from the common electron ionization (EI) or chemical ionization (CI) ion sources which are characterized in general by the Maxwellian velocity distribution. In contrast, the distribution of initial velocities in an API ion source occurs during the free-jet expansion of ions into the vacuum through the nozzle 66. This distribution in initial ion velocities is related primarily to the aerodynamic properties of the sampling nozzle, its geometry and the pressure in the first vacuum region.

There are few data in the literature relating the geometry of an ion sampling nozzle to the energy distributions of the particles expanding into the vacuum from the supersonic jet expansion region. However, it has been empirically established that a narrowed energy distribution (maximum density of the particle in phase space or bright ion source) is achieved when the aspect ratio is 0/3 (nozzle diameter/nozzle thickness), as illustrated for nozzle plate 64. Expansion of the electrospray 84 into the vacuum 18 through such a nozzle is characterized by velocity equalization of all species in the jet rather than a Maxwellian distribution. This implies that the heavier organic ions are traveling at the same velocity as the much lighter air molecules. Thus, the kinetic energy of the ions is higher, by the average mass ratio (ions/air), than is the thermal energy, and apparently can reach values of several eV. The equalization of velocities in the jet occurs in a region that has been named the "silent zone", which is generally indicated at 130 (FIG. 1 and FIG. 4) and which has a characteristic distance $Z_m$ from the opening of the nozzle 66. This distance is usually referred to in the literature as the Mach distance or Mach disk and is given by:

$$Z_m = 0.67 \, d_O \, (P_1)^{-\frac{1}{2}} \tag{4}$$

where $d_0$ is the nozzle diameter.

In the region 130 between the nozzle and Mach disk, aerodynamic forces accelerate ions. After ions pass through the Mach disk one can consider them under vacuum conditions and any subsequent scattering of ions from the beam is attributable to their colliding with residual gas molecules or friction forces.

In two stage API sampling systems such as the interface 10, there are two types of systems by which ions may be transported to the mass analyzer region. They are classified by the position of the separating diaphragm 100 with respect to the Mach disk region. The first type positions the separating diaphragm inside the Mach disk region. In this configuration the aerodynamic expansion of gas into the vacuum chamber 18 is used to then transfer ions into the mass analyzing vacuum chamber 20. The consequent sampling of ions from the "silent zone" 130 is efficient because ions and gas are moving at equal speeds in the same direction, resulting in minimal scattering of the ion beam. Disadvantages include: (1) cluster ion formation which results from the strong and rapid cooling of the gas upon expansion; (2) the requirement for high pumping speeds in both the first and the mass analyzed regions, and (3) the separating diaphragm must be extremely sharp (ideally zero thickness) with no imperfections in order to minimize disturbances of the ion beam.

The second type of two-stage API sampling system is illustrated in FIGS. 1 and 4, wherein the separating diaphragm 100 is situated outside the Mach disk region so the requirements for high pumping speed are significantly alleviated. In this preferred configuration, the separator diaphragm 100 and the extraction lenses 80, 90 and 92 are used to extract ions from the supersonic jet entering region 18 to transport them to the mass analyzing region 20. A flat separator diaphragm 100 is used rather than a "skimmer" because a separator diaphragm is easier to construct and implement into the sampling region of the mass analyzer and also because the separator diaphragm allows more direct control over ion motion and easier optimization of ion optics. In the case of a skimmer, the electrical field produced by the ion optics does not penetrate into the skimmer cone. As a consequence it is difficult to control the ion motion inside the skimmer by an electrical field and thus it is nearly impossible to optimize ion optics.

The optimization of ion optics in the first vacuum region 18 is complicated by the presence of aerodynamic forces. Since these forces are nonconservative, one cannot apply the space theory for optimization of ion optics unless several assumptions are made. The following are the principle assumptions used in the below calculations: (1) all species in the supersonic jet have reached an equilibrium velocity at the nozzle opening; (2) maximum ion transmission (maximum brightness of ion source) corresponds to the situation where the first focal point of the ion optical system coincides with the Mach disk distance; (3) ion optics after the Mach disk region should provide continuous acceleration of the ion beam to compensate for frictional effects attributable to ion-neutral collisions in the first vacuum region. Based on the above assumptions, a standard electrostatic field and ion motion simulation program was used for calculating ion trajectories in the first vacuum region. Since the simulation program does not take into account aerodynamic forces, the kinetic energy of the ions was assigned a value of 2-5 eV at the entrance of the ion optical system. The only undetermined parameter for the optimization is the potential difference across the first vacuum region. It was given a value of 50 V which is a typical value used in various API interfaces when operated under "mild" CID conditions.

The ion motion simulation program, SIMION (D. A. Dahl, J. E. Delmore, SIMION PC/PSZ version 4.02, National Engineering Laboratory) was used to analyze and optimize the ion optical system. Since the electric field depends upon the potential difference between the lenses in the first vacuum region (rather than absolute value of the potential), the lens stack 80, 90 and 92 is considered to be "floated" at a potential U. The value of this optimization, along with the calculated ion trajectories 132 and a map of the equipotential lines 134, are shown in FIG. 4. The first lens electrode 80 provides ion focusing with a focal point situated directly in the Mach disk region 116 while the remaining lenses 90 and 92 and the diaphragm 100 provide a continuous acceleration of the ions to compensate for frictional forces and to produce a low divergence ion beam. This ion optics arrangement may be termed an "electrical skimmer" geometry. The kinetic energy of the ions exiting the first vacuum region 18 was assumed to be the product of the electric field force at the exit of the ion optical system and the mean free path of the ions. The determination of this parameter is critically important for the optimization of ion optics in the mass analyzer vacuum region. Under typical operating conditions a good estimation of this energy corresponds to the acceleration of ions between electrodes 92 and 100 and is given by their potential difference.

Figure 5:
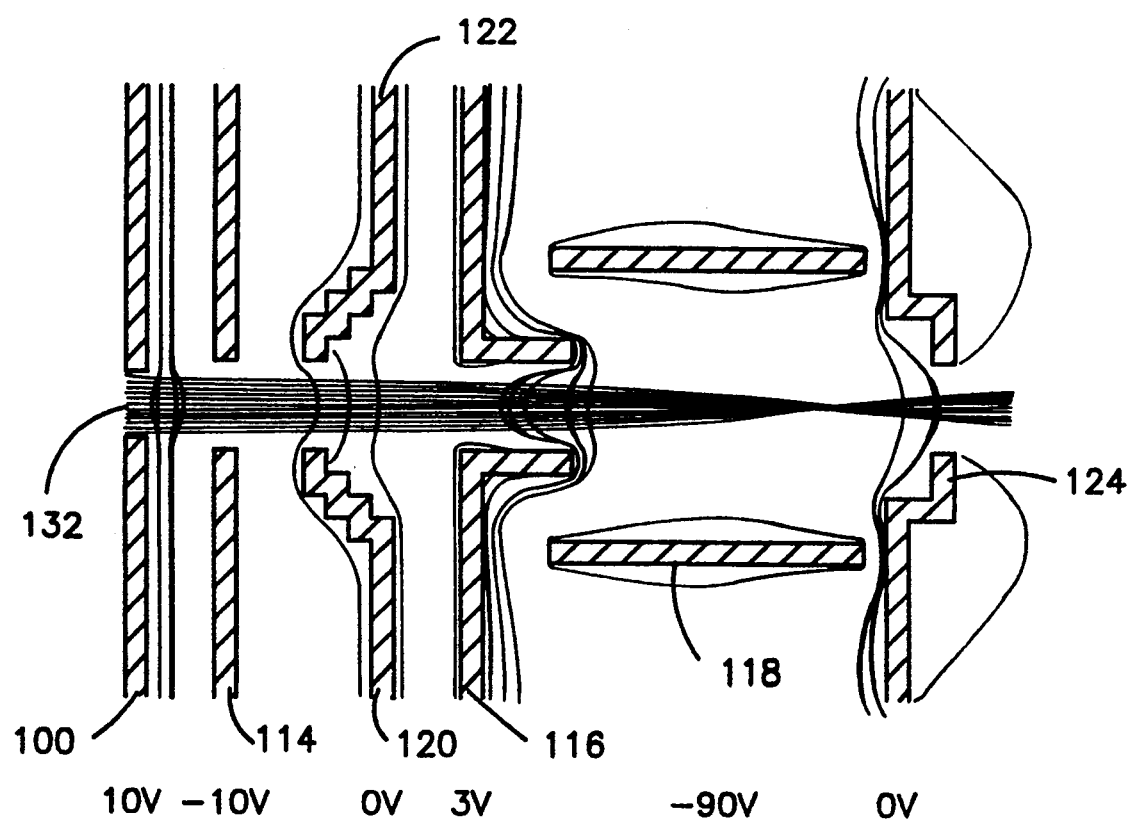
FIG. 5 is a plot of the electrostatic field and ion trajectories in a second vacuum region of the apparatus of FIG. 2.

The calculation of ion optics in the second vacuum region 20 is based directly on phase space theory. According to this theory the maximum efficiency of an ion optical system is achieved when the transformation of the ion emittance from the first vacuum region 18 matches the acceptance of the ion trap. Comparison of the energy coordinates for ion trap acceptance and ion kinetic energy at the exit of the first vacuum region gives a value for the floating potential (U) of the first vacuum region:

$$U = D - (V_{92} - V_{100}) \tag{5}$$

where $V_{92}$ is the potential on electrode 92 and $V_{100}$ is the potential on diaphragm 100. Under typical operational conditions the value of U is 10 V. Using this value for the potential of the separating diaphragm one can use the SIMION program to design an ion optical system for the second vacuum region which will have its focal point situated at the entrance aperture of the ion trap. The results of this SIMION analysis are shown in FIG. 5. The diaphragm 100 and the lens 114 serve as a prefocusing stage for the ion beam 132, while the deflector electrodes 120 and 122 serve as an ion gating assembly. The deflector electrodes are represented as two separate angled plates 120 and 122 and are grounded during the passage of ions into the ion trap for accumulation. During ion detection the ion beam is gated by pulsing one of the deflector electrodes to 100 V to deflect the beam away from the ion trap entrance aperture. Lenses 116 and 118 serve as a short focus tubular lens array which has a focal point situated near the entrance aperture 124 of the ion trap.

Summarizing the previous calculations, the following preferred set of voltages for ion transmission (first and mass analyzer regions) are obtained: $V_{60}=60$ V; $V_{80}=70$ V; $V_{90}=40$ V; $V_{92}=20$ V; $V_{100}=10$ V; $V_{114}=-10$ V; $V_{116}=3$ V; $V_{118}=-90$ V, where the subscript identifies the electrode.

To test the sensitivity, mass resolution, and mass assignment of the present instrument, simple infusion experiments were conducted in which a solution of known composition was delivered to the device of FIG. 1 at a fixed flow rate. A conventional pneumatically assisted electrospray apparatus 22 was used to produce a spray of charged solvent droplets. The sprayer, which was typically maintained at +3 kV for the production of positive ions, consisted of an inner, 5 cm long stainless steel capillary 132 (150 mm ID) for the liquid transfer capillary and a larger stainless steel outer capillary 134 (340 mm ID). The outer capillary was, concentric to the inner capillary, and was used for introduction of a carrier gas ($N_2$) which was maintained at a pressure of 60 psi. All data were acquired under pneumatically assisted nebulization electrospray conditions. In all experiments the sprayer was positioned about 1 cm away from the liquid shield lens 60. For maximum sensitivity, the sprayer position was tuned for maximum total ion current of infused analyte ions. A micro syringe pump (Model 22, Harvard Apparatus, S. Natick, Ma.) was used for sample delivery, usually at a flow of 4 microliters per minute.

Figure 6:
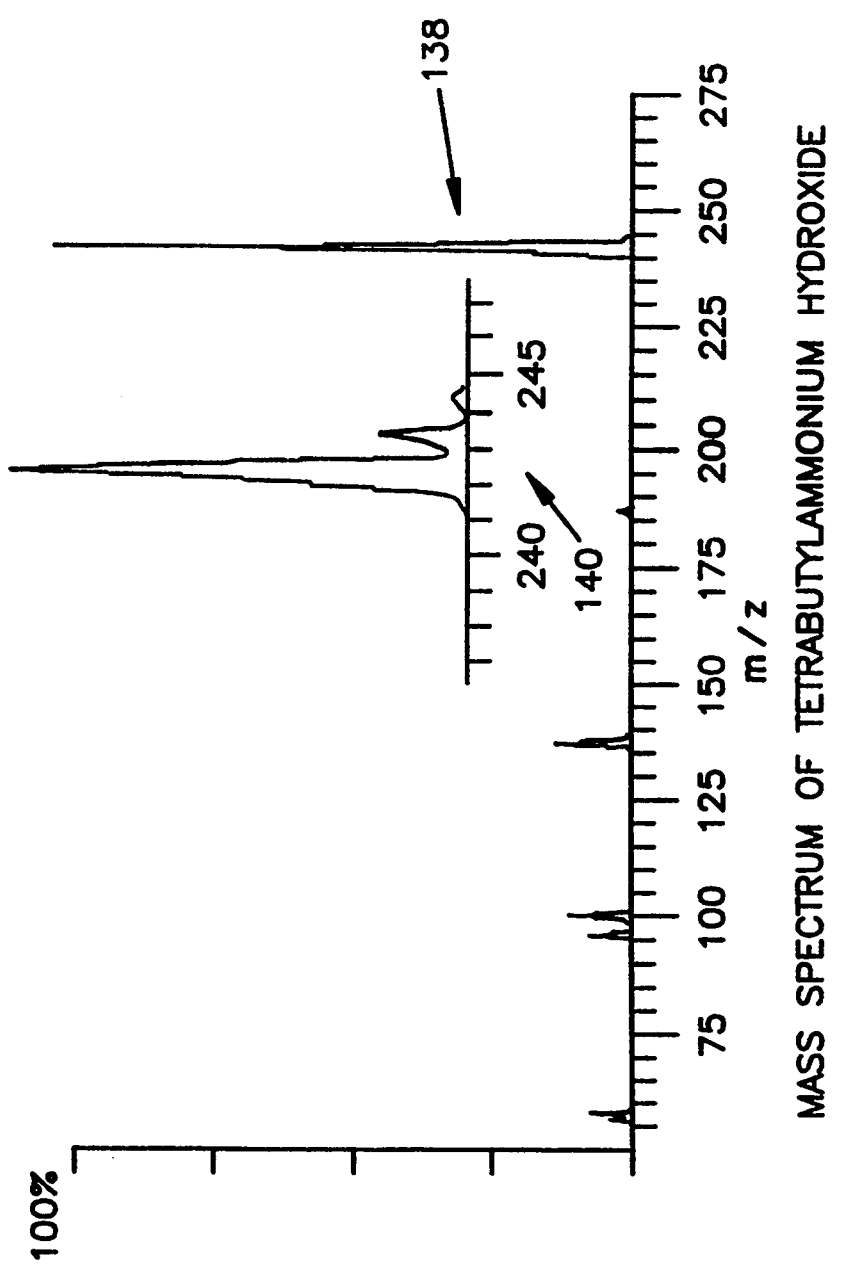
FIG. 6 is a plot of the mass spectrum of tetrabutylammonium hydroxide (TBAH) with mild declustering energy, obtained using the apparatus of FIG. 1.

Tetrabutylammonium hydroxide (TBAH), a tetraalkyl quaternary amine, was chosen for these studies because it is extremely sensitive to electrospray ionization and produces a well characterized and reproducible mass spectrum under CID conditions. A typical spectrum from 10 pmol/$\mu$L TBAH in methanol, obtained under mild declustering conditions is shown in FIG. 6. The actual potential difference across the first vacuum region was 50 V ($V_{64}-V_{100}$). As observed from FIG. 6 the base peak 138 in the mass spectrum corresponds to the molecular ion of TBAH (m/z=242). The less abundant ions at m/z=100 and 142 are fragments of TBAH and arise from the mild CID conditions used in this experiment. Resolution of the $^{12}$C and $^{13}$C isotopes of TBAH (molecular ion) is illustrated in the inset 140 of FIG. 6. The empirically determined voltages which led to the maximum ion current were: $V_{50}=60$ V, $V_{60}=65$ V, $V_{70}=46$ V, $V_{72}=25$ V, $V_{80}=10$ V, $V_{94}=-14$ V, $V_{96}=7$ V and $V_{98}=-110$ V. The efficiency of the ion optic system was checked by removal of the lens 80 and readjustment of the potentials for maximum total ion current. Removal of lens 80 led to a six fold reduction in total ion current.

Figure 7:
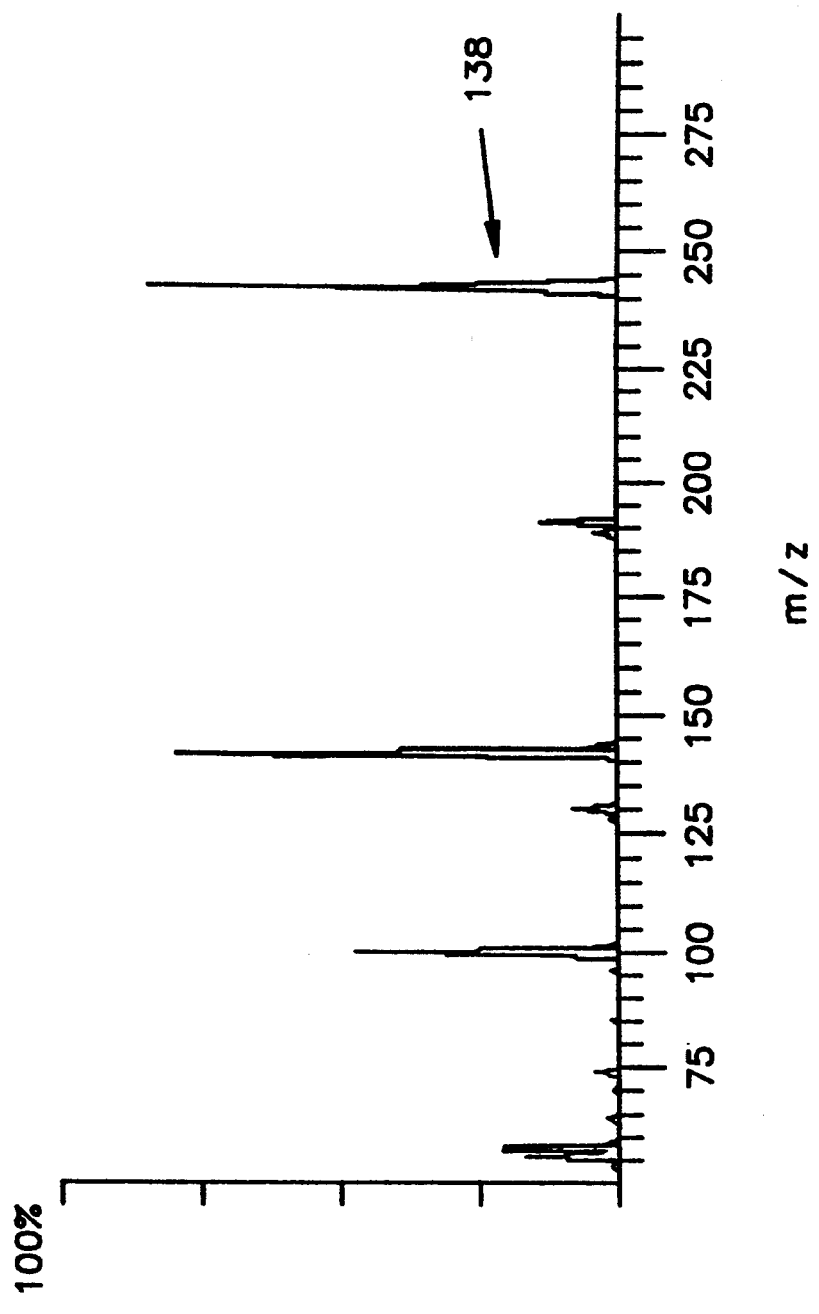
FIG. 7 is a plot of the mass spectrum of TBAH with "up front" CID obtained using the apparatus of FIG. 1.

When attempting to identify an unknown compound it is often desirable not only to obtain its molecular weight, but also to obtain structural information concerning it. One way this can be achieved in electrospray is by adjusting the potential drop across the first vacuum region. This is often referred to as "up-front" CID, and the results are clearly illustrated in FIG. 7. In this example a potential drop of 65 V across the first vacuum region was applied to induce fragmentation of TBAH (10 pmol/$\mu$l). Although the molecular ion (m/z=242) is still the base peak at 138, other structurally informative ions are present at m/z=57, 100, 142 and 186.

Figure 8:
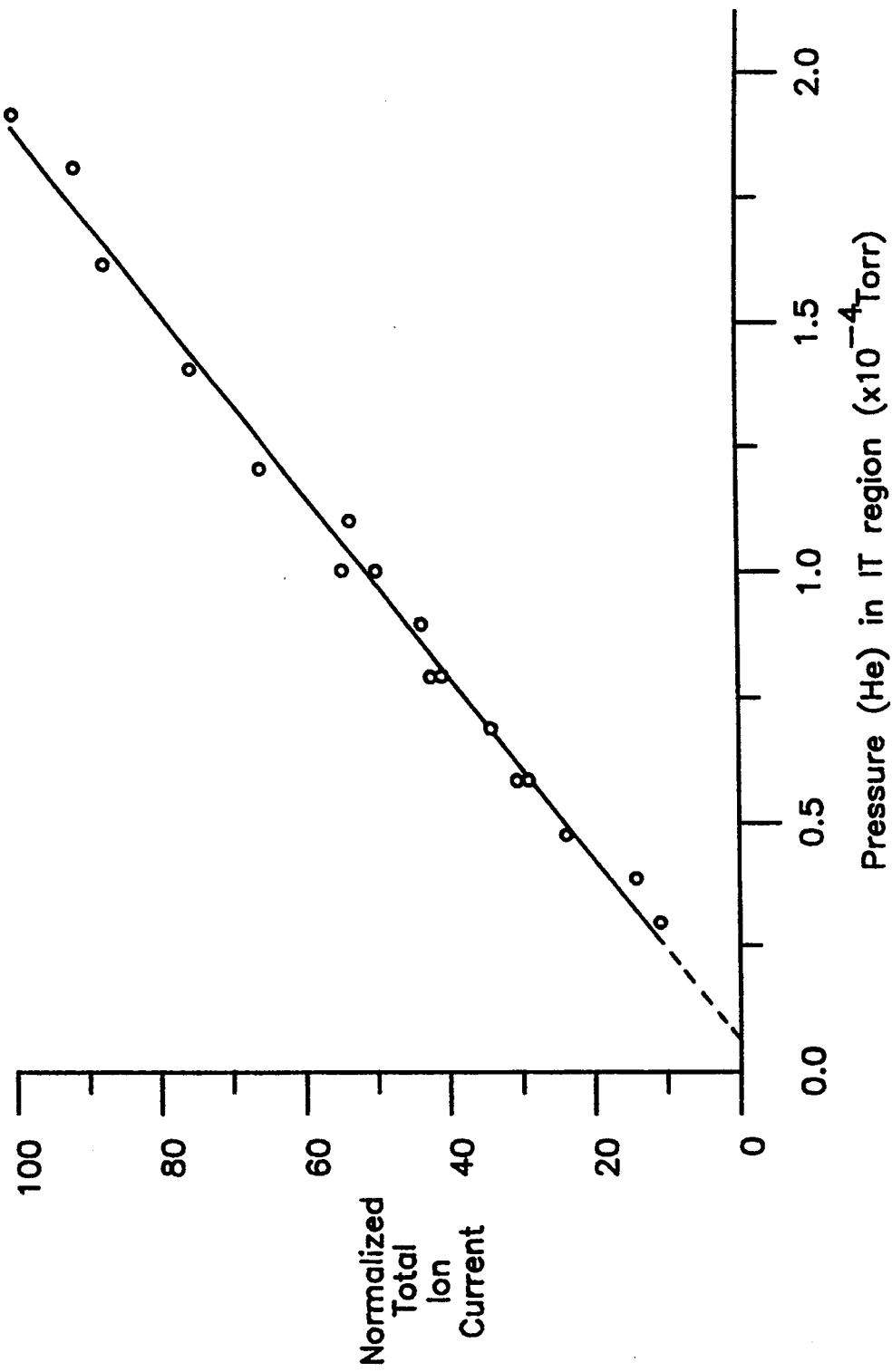
FIG. 8 is a plot of the relationship between total ion current and the pressure of damping gas (He) in the ion trap apparatus of FIG. 1.

Experimental conditions leading to confinement of externally produced ions in the ion trap were also studied. FIG. 8 shows the dependence of total ion current on the pressure of the helium damping gas in the ion trap, obtained by a direct reading from an ionization type nanometer. The ability of the trap to capture externally produced ions increased linearly with pressure. This linearity is in excellent agreement with the above-described mechanism of collisional relaxation for capturing ions (see eq. 3). Residual gas molecules are thought to be responsible for the scattering of ions in the absence of He damping gas. This is believed to be the reason why the line does not pass through the origin in FIG. 8. The upper range of pressure in this experiment was limited to 0.2 mTorr because low pressure must be maintained in the mass analyzer region of the ion trap for normal functioning of the electron multiplier.

The liquid shield lens 60 incorporated in the atmospheric pressure region of the electrospray interface in accordance with the present invention significantly decreases the number of spikes in the total ion current, and improves the analytical ruggedness of the interface. Before incorporation of this lens the nozzle 66 required cleaning after approximately one hour of operation at high flow rates (>50 $\mu$l/min), but after installation of the liquid shield lens 60 this problem was alleviated, even at flow rates up to 1.5 ml/min.

There are several theoretical models which describe the formation of ions by electrospray ionization. Although these models differ, they do agree that the mechanism of ion formation involves at least two stages: (1) formation of charged droplets from the sprayer; and (2) gas phase ion formation from these small, charged droplets. It is believed that the liquid shield lens 60 aids in the process of enabling ions to escape into the gas phase from the charged droplets. The shield also appears to protect the sampling nozzle from accidental plugging or restriction by liquid droplets and particles by inhibiting the larger droplets from coming into contact with the nozzle.

Figure 9:
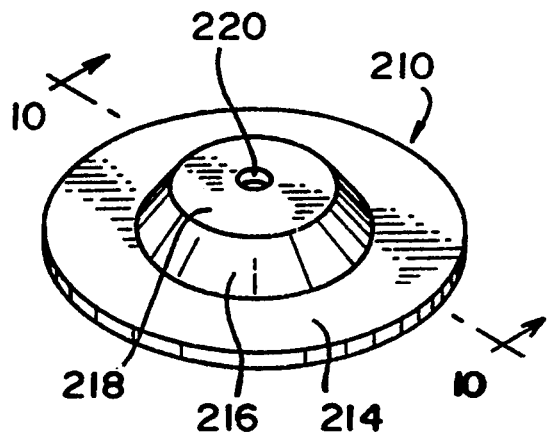
FIG. 9 is a perspective, diagrammatic illustration of a second embodiment of the liquid shield of the present invention.
Figure 10:
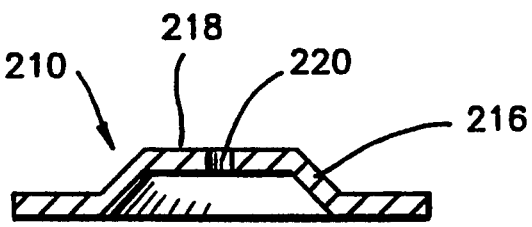
FIG. 10 is a cross-sectional view of the shield of FIG. 9, taken along lines 10—10.

The liquid shield 60 is metal; for example, stainless steel, and is illustrated in FIGS. 1 and 2 as being generally disk-shaped, with the upwardly and outwardly extending peripheral flange 74 providing a mounting surface for engaging the top of the support flange 68 of nozzle plate 64. However, it will be understood that the shield can take other forms without adversely affecting its shielding performance. For example, the shield can be in the form of a flat disk, with its periphery resting on top of flange 68 or on a suitable shoulder formed on the nozzle plate and located to space the shield 60 above the plate by a suitable distance. Another alternative is illustrated in FIGS. 9 and 10, where a stainless steel shield 150 includes a flat base portion 152 and an upstanding central mesa portion 154 in which an aperture 156 is formed. The central portion 154 may be conical, as illustrated, or may be cylindrical, and may enclose the heater coils 78, if desired. The outer edge of the disk portion 152 may rest on flange portion 68 of the nozzle plate, or may rest on the top surface of plate 64, to provide the required space between aperture 156 and nozzle 66.

As indicated above, the liquid shield of the present invention can be used with the interfaces to a variety of mass analyzers, in addition to the ion trap device described above. For example, the shield has also been used with quadrupole mass analyzers for liquid chromatography mass spectrometry (LC/MS) utilizing conventional high pressure liquid chromatography (HPLC) flow rates. Such systems are illustrated in FIGS. 11 and 12 as additional embodiments of the present invention.

Figure 11:
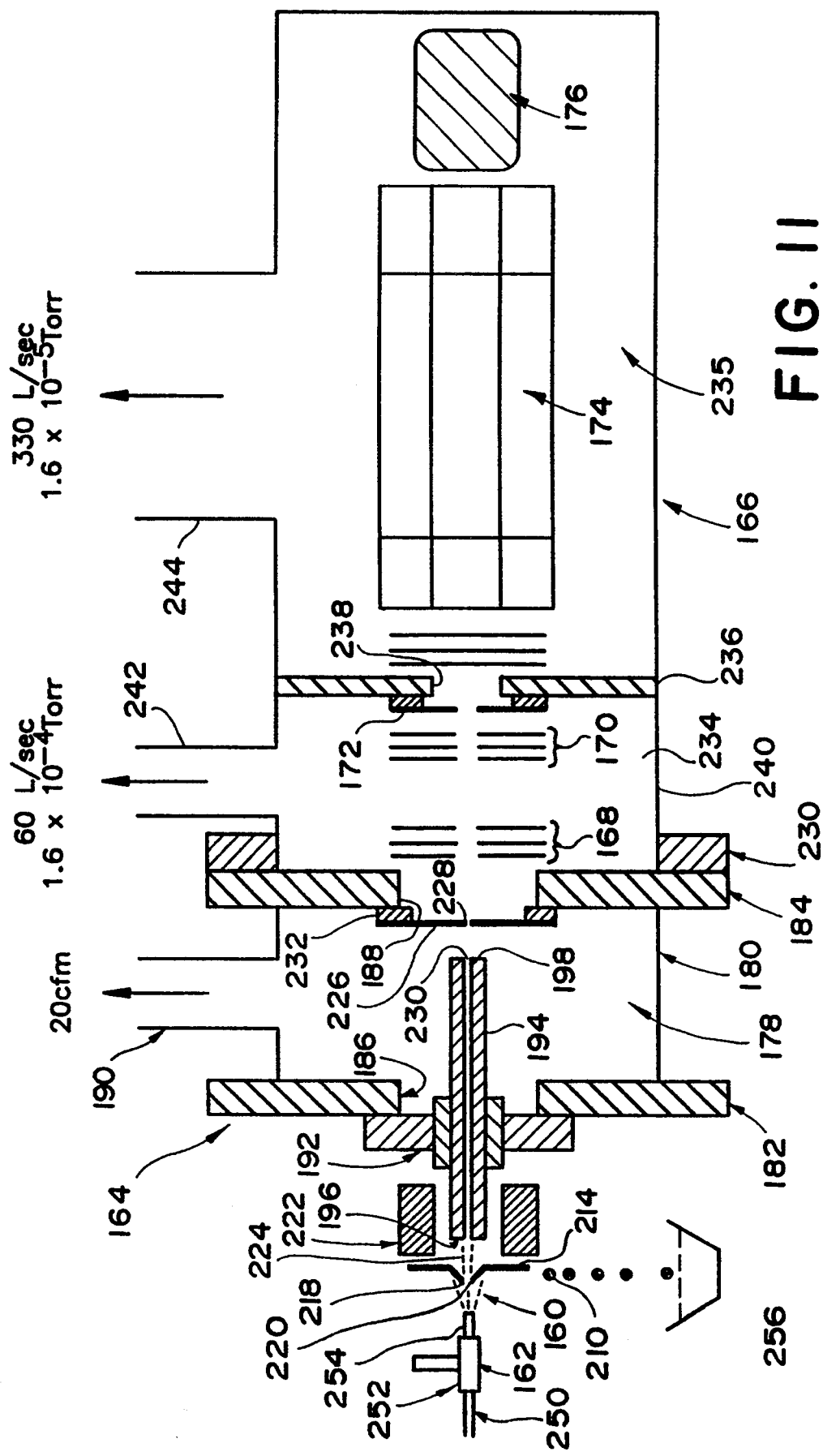
FIG. 11 is a diagrammatic illustration, in cross-section, of an atmospheric pressure ionization sampling device for a quadrupole mass spectrometer, utilizing the liquid lens shield of the present invention.
Figure 12:
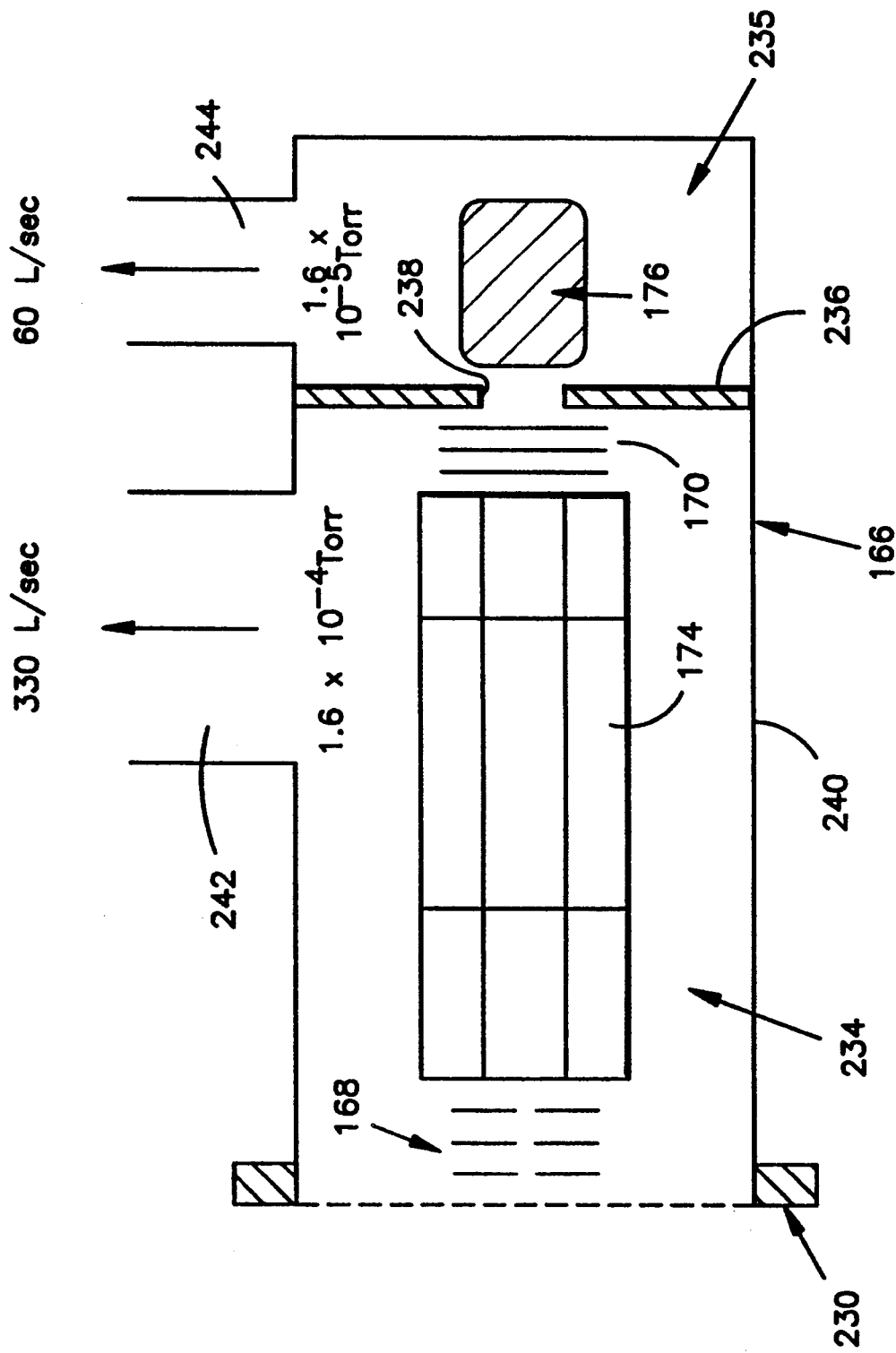
FIG. 12 is a diagrammatic illustration, in cross-section, of a quadrupole mass spectrometer system for use with the liquid shield API interface of the present invention, comprising two stages of vacuum pumping wherein the quadrupole mass analyzer is placed in a first mass analyzer vacuum stage while the electron multiplier detector is situated in a second vacuum stage.

In accordance with the embodiment of FIG. 11, ions 160 are supplied from a source 162 through an interface generally indicated at 164 to a mass analyzer 166, the interface serving to sample ions at atmospheric pressure for delivery to the analyzer. The mass analyzer 166 may be a Hewlett Packard Model 5985B mass spectrometer having an associated Einzel lens system 168, 170, 172, a quadrupole mass analyzer 174, and an electron multiplier detector 176, with its standard electron ionization source being replaced by the interface 164. The interface vacuum region is illustrated at 178 and may be formed by a cylindrical housing 180 constructed from stainless steel pipe. The housing is connected to front and rear flanges 182 and 184 which incorporate axial apertures 186 and 188, respectively. A vacuum seal is provided between the housing 180 and the flanges, and a vacuum port 190 provides attachment for a vacuum line from a suitable vacuum pump such as a 400 liter per minute Model D16A rotary pump furnished by Leibold-Heraeus Vacuum Products, Inc.

A nylon bulkhead union 192 such as a Swagelok, provided by Crawford Fitting Company, Solon, Ohio, is fitted in the aperture 186 of flange 182 to provide an electrically isolated, adjustable feed through which secures a stainless steel ion sampling capillary 194. The capillary may be a tube having a 0.5 mm inner diameter and a 6.35 mm outer diameter, and may be, for example, 25 cm in length, extending out of union 192 toward source 162 at its outer end 196 and extending into vacuum region 178 at its inner end 198.

In accordance with the present invention, a grounded liquid shield lens 210 is provided at the front end 196 of the ion sampling capillary 194. The shield 210 may be similar to that illustrated in FIG. 2, but for purposes of illustration, is shown as being similar to the shield of FIGS. 9 and 10. Thus, it is illustrated as having a stainless steel disk portion 214 which may be 1.3 mm thick and 3.8 cm in diameter, and is further shown with a conical orifice 216 which may be 6.4 mm in diameter at its base, with a height of 5.1 mm and a 4 mm diameter top surface 218 with a 2 mm diameter aperture 220. Typically, the distance between the liquid shield 210 and the outer, or entry end 196 of the capillary 194 is 5 mm. The liquid shield preferably is electrically grounded, although a small potential can be applied to it for optimal sensitivity, and it can be mounted with a Teflon support (not shown) to insulate it from the flange 182.

A heater 222 is incorporated in the open atmosphere region 224 between the liquid shield 210 and the end 196 of the ion sampling capillary to alleviate ion formation from liquid microdroplets. A variable DC power supply is also connected to the electrically conductive ion sampling capillary 194 to control its electrical potential, the potential preferably being variable between zero and 250 volts.

Adjacent the vacuum end 198 of the ion sampling capillary is a flat diaphragm 226 having a central orifice 228 aligned with the central opening 230 of the capillary 194. Interface flange 184 is machined at aperture 188 to accommodate the flat diaphragm 226 and is also shaped to receive the mass analyzer vacuum system mounting flange 230. The diaphragm may be mounted on the flange and electrically isolated therefrom by a polyethylene insulator disk 232. The distance between the end 198 of the ion sampling capillary and the flat diaphragm 226 is typically 4 mm. The potential of diaphragm 226 is controlled between zero and 12.5 volts.

The transmission of ions to the mass analyzer 166 from the capillary 194 is achieved using the two sets of Einzel lenses 168 and 170 placed in tandem between the ion separating diaphragm 226 and the mass analyzer 166. The mass analyzer incorporates two vacuum chambers 234 and 235, which are separated by a flange 236 having a central aperture 238 which serves as the entrance to analyzer 174. The Einzel lenses 168 and 170 are located in the second vacuum chamber 234, between flanges 184 and 236. The vacuum chambers are formed by a stainless steel pipe 240, which is fixed to flange 230 and secured thereby to interface 164. Pipe 240 includes vacuum ports 242 and 244 connected to suitable vacuum sources (not shown).

Eluant from a liquid chromatography (LC) column (not shown) travels at a rate of from 10 to 1,500 microliters/min. through a connecting silica capillary 200 in the ion spray source 162 and is directed toward the inlet end 196 of the capillary 194 housed in the liquid shield API/MS interface 164. A stainless steel outer capillary 252 surrounds the silica capillary 250 and a high voltage, in the range of 3 to 5 kV, is applied thereto by way of an electrical contact so as to apply the high voltage to the effluent near the outlet spray tip 254 of the source 162. Nitrogen carrier gas is passed through the annular space between the inner and outer capillaries 250 and 252 at, for example, 50 to 80 psi to focus, carry, and direct spray toward the liquid shield. The spray tip 254 may be positioned off center by about 5 mm with respect to the aperture 220 of the liquid shield 210, and about 10 mm distant therefrom. Excess eluant is allowed to drip from the liquid shield into a beaker 256.

The two-stage mass analyzing vacuum system for a quadrupole mass analyzer in the foregoing embodiment can be also arranged alternatively as shown in FIG. 12. In this alternative, the quadrupole mass analyzer 174 is situated in chamber 234 of the mass analyzer vacuum system 166, while the electron multiplier detector 176 is placed in vacuum chamber 235. The Einzel lenses 168 and 170 are located in chamber 234, which has its vacuum port 242 connected to a suitable vacuum source (not shown). Vacuum region 235 similarly has a vacuum port 244 connected to a suitable vacuum source (not shown). The two vacuum chambers are separated by the flange 236 with its central aperture 238, providing ion exit from the quadrupole mass analyzer to an electron multiplier. The central aperture 238 is typically in the range from 1 mm to 10 mm in diameter, the size being determined from the pressure requirements in the vacuum regions for normal operation of the mass analyzer and the electron multiplier detector. The typical operational pressure of the system is $1.6 \times 10^{-4}$ torr for the vacuum region 234 and $1.6 \times 10^{-5}$ Torr for the vacuum region 235. The electron multiplier 176 could be a standard Galileo 4762 HED detector. The flange 230 is the API interface mounting flange of the mass analyzing vacuum system. It might be machined to accommodate either the API interface shown in FIG. 1 with an ion trap mass analyzer or the interface shown in FIG. 12 with a quadrupole mass analyzing instrument. The vacuum system presented in FIG. 11 allows the introduction of more ions into the mass analyzer than a standard Hewlett Packard Model 5985B mass spectrometer vacuum system, thus providing better sensitivity.

Figure 13:
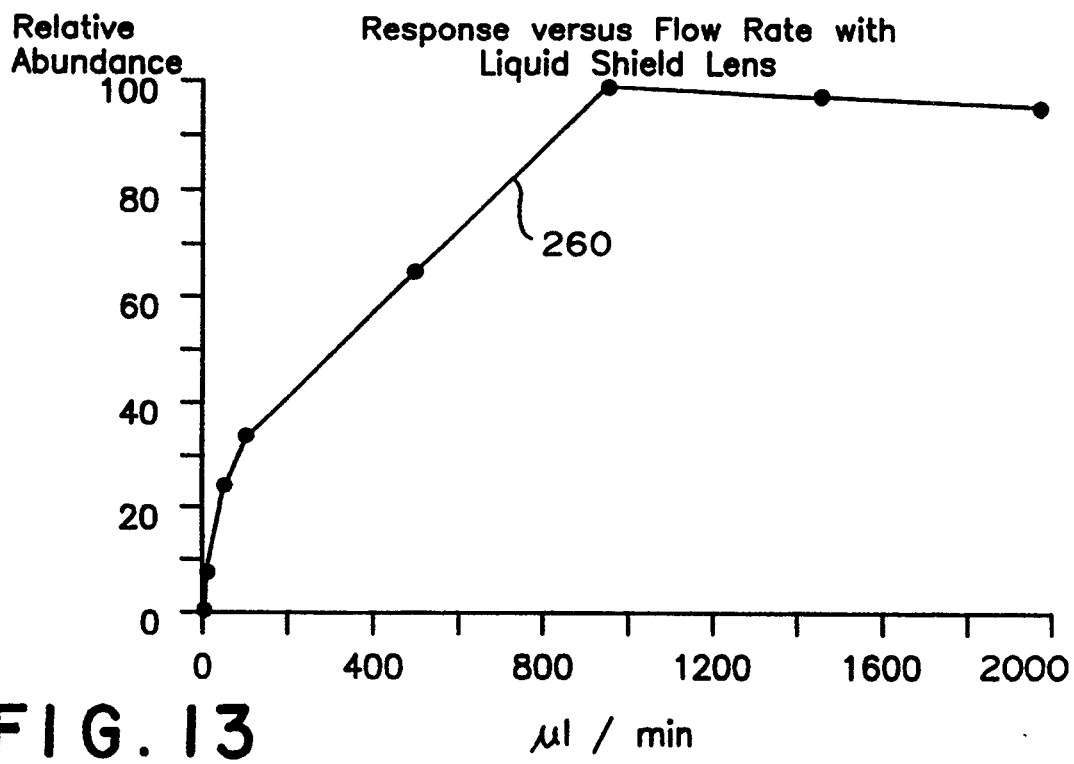
FIG. 13 is a plot of the mass spectrometer output signal versus spray flow rate obtained using the apparatus of FIG. 11.
Figure 14:
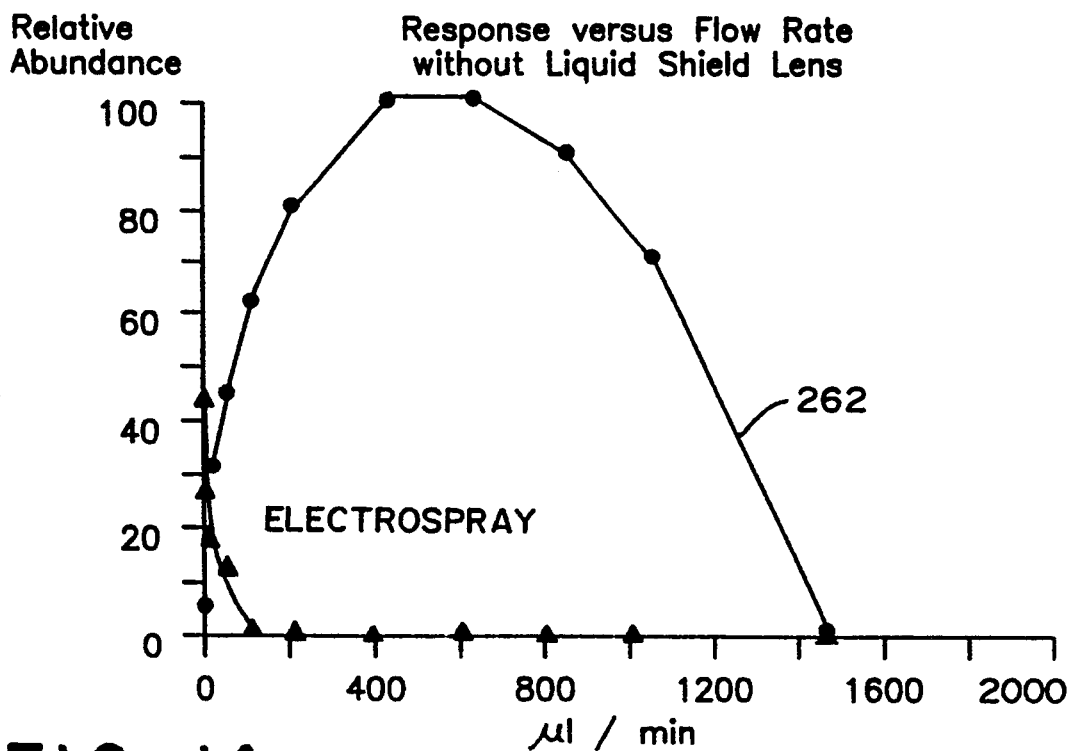
FIG. 14 is a plot of the mass spectrometer output signal versus ion spray flow rate in the absence of the liquid shield of the present invention.

In FIG. 13, graph 260 represents the mass spectrometric response versus flow rate for m/z 242 TBAH, using the liquid shield 210 placed between the spray source 150 and the ion sampling capillary 194, in the manner illustrated in FIG. 11. This simple shield allows the use of liquid flow rates ranging from a few microliters per minute to 2 milliliters per minute while producing a stable ion current signal and good sensitivity. The liquid shield is grounded and acts as a spray splitting device, keeping excess liquid away from the ion sampling capillary orifice, as discussed above. It also appears that the shield may aid in the desolvation process where the droplets reduce in size before the charged analyte escapes into the gas phase. The shield also prevents accidental obstruction of the ion sampling capillary by larger liquid droplets which cause instability in the ion current signal as well as decreased sensitivity at high flow rates, as is illustrated in FIG. 14 by curve 262. This curve illustrates the mass spectrometric response versus flow rate with the liquid shield removed.

To test the ruggedness and utility of the present invention as an on-line detector, a series of experiments were conducted coupling high performance liquid chromatography (HPLC) to the ion trap and quadrupole mass analyzers through the interfaces described above. The compounds chosen for these studies were small quaternary ammonium drugs. These charged compounds were chosen because this class of drugs is not amenable to gas chromatographic analysis (GC) without pyrolysis, so the combination of liquid chromatography or capillary electrophoresis with mass spectrometry may provide a preferred tool for their identification at the low nanogram level.

Liquid chromatography/mass spectrometry quadrupole mass analysis of the quaternary ammonium drugs was performed on a 4.6 mm i.d.×150 mm Zorbax SB-CN C8 column packed with 5 µm particles. The LC buffer was delivered by a Hitachi L-6200A Dump (Hitachi, Ltd.) at a flow rate of 1.2 mL/min without post-column using an internal loop injector of 5 µL, model 7125 (Rheodyne). Isocratic elution of the quaternary ammonium drug compounds was obtained using a mixture of acetonitrile/water (80:20) which contained 5 mM ammonium acetate. The buffer solution was degassed prior to use by sparging with helium.

Figure 15:
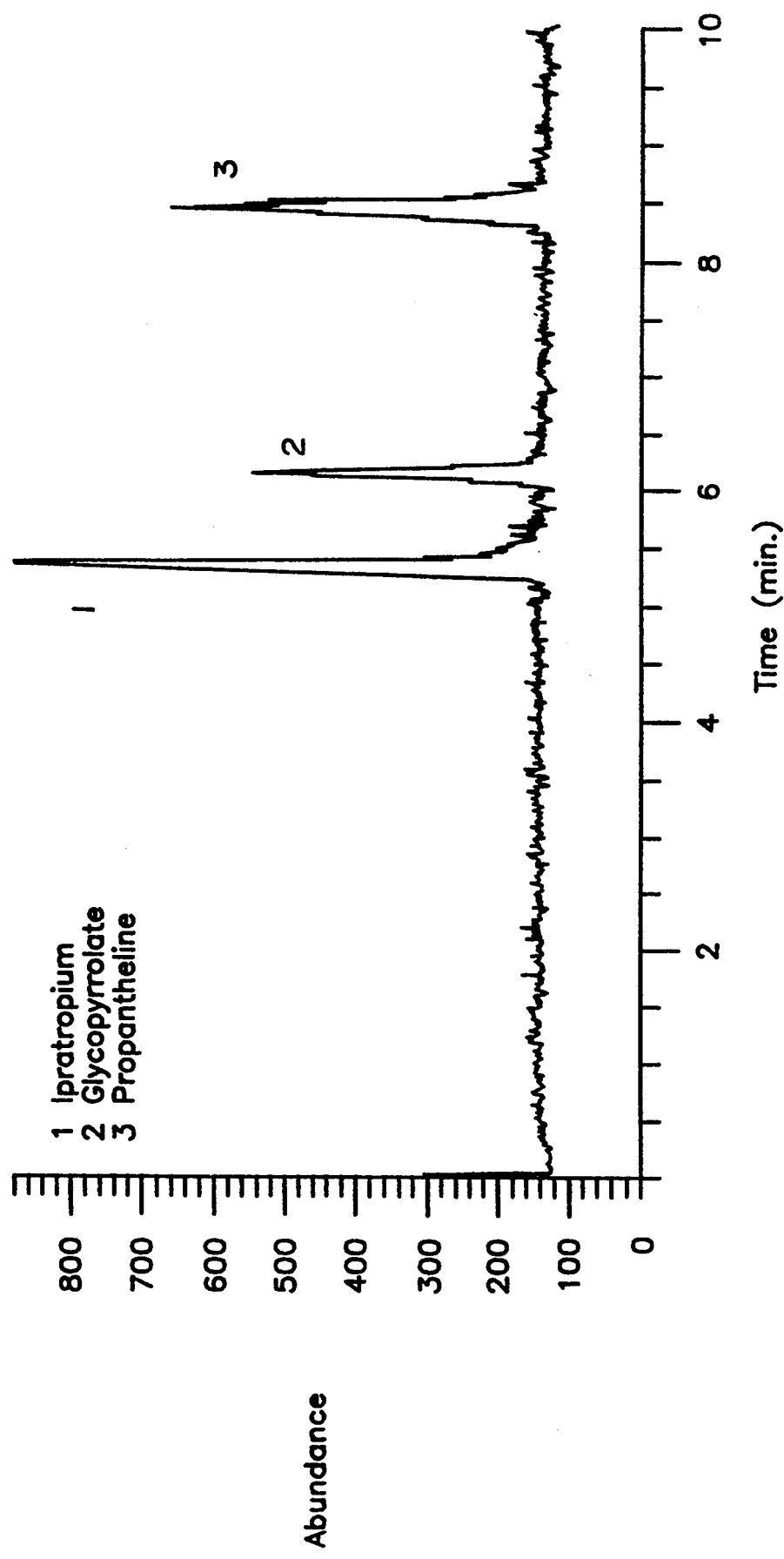
FIG. 15 is a plot of selected ion monitoring MPLC-MS analysis of a synthetic mixture containing 250 pg each of four quaternary ammonium compounds, obtained using the apparatus of FIG. 11.

Results of the on-line coupling of HPLC to the apparatus of FIG. 11 mass spectrometer of the present invention are shown in FIG. 15. A synthetic mixture containing 250 pg of each drug was injected on-column under standard HPLC conditions. The total column effluent (1.2 mL/min) was directed to the mass spectrometer via the liquid shield in this experiment. The selected ion monitoring results shown in FIG. 15 clearly identify the molecular ions of the injected compounds.

Liquid chromatographic/ mass spectrometry (LC/MS) micro bore HPLC ion trap mass analysis of the quaternary ammonium drugs was performed on a 1 mm i.d.×100 mm Spherisorb $C_8$ (Isco) column packed with 3 µm particles. The LC buffer was delivered by a Hitachi L-6200A pump (Hitachi, Ltd.) at a flow rate of 40 mL/min without post-column splitting. Compounds of interest were loaded into the HPLC column using an internal loop injector of 0.5 µL, model 7520 (Rheodyne). Isocratic elution of the quaternary ammonium drug compounds was obtained using a mixture of acetonitrile/water (80:20) which contained 20 mM ammonium acetate and 0.15% trifluoroacetic acid. The buffer solution was degassed prior to use by sparging with helium.

Figure 16:
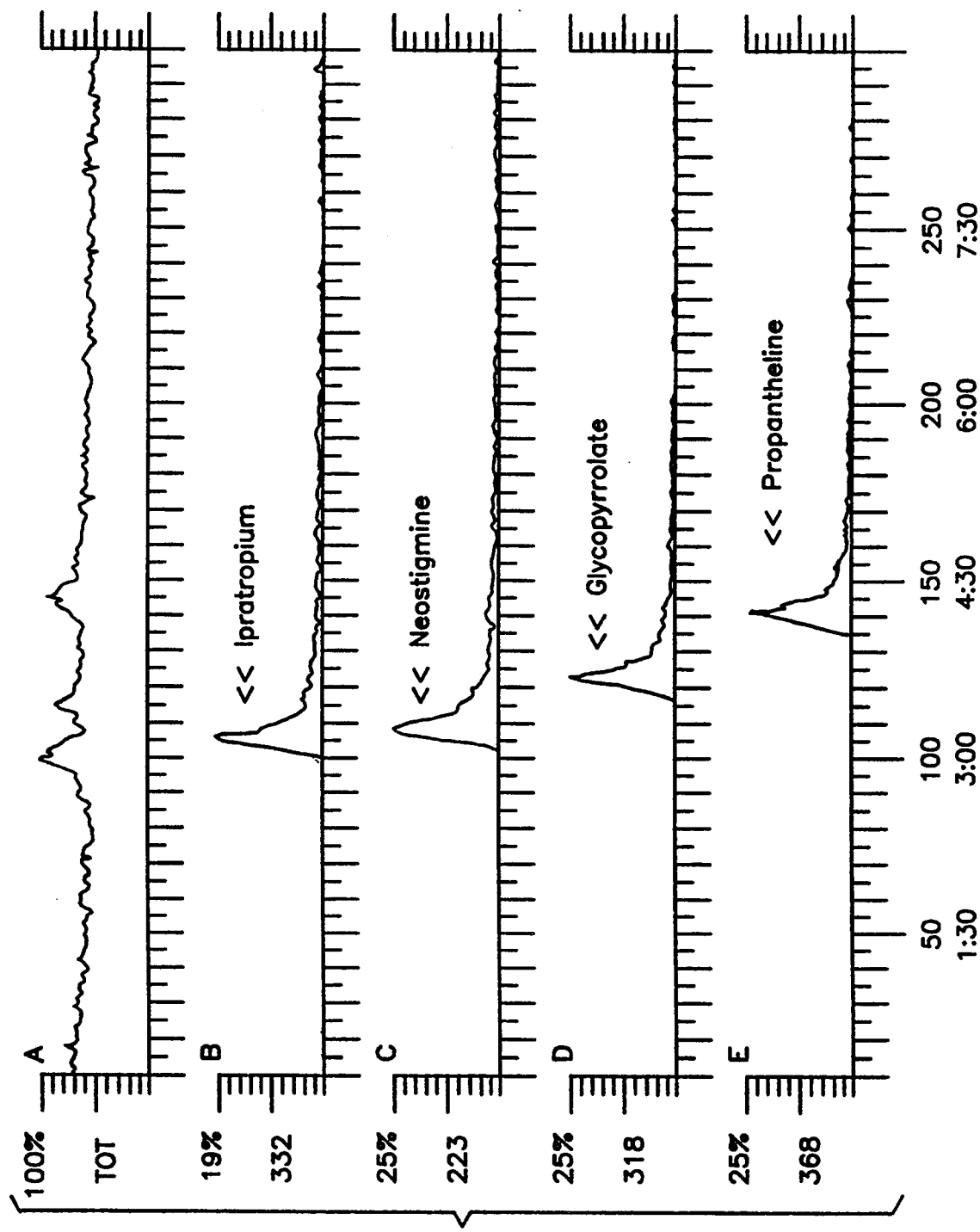
FIG. 16 is a plot of HPLC-ion trap MS full-scan analysis of a synthetic mixture containing 5 ng each of four quaternary ammonium compounds, obtained using the apparatus of FIG. 1.
Figure 17:
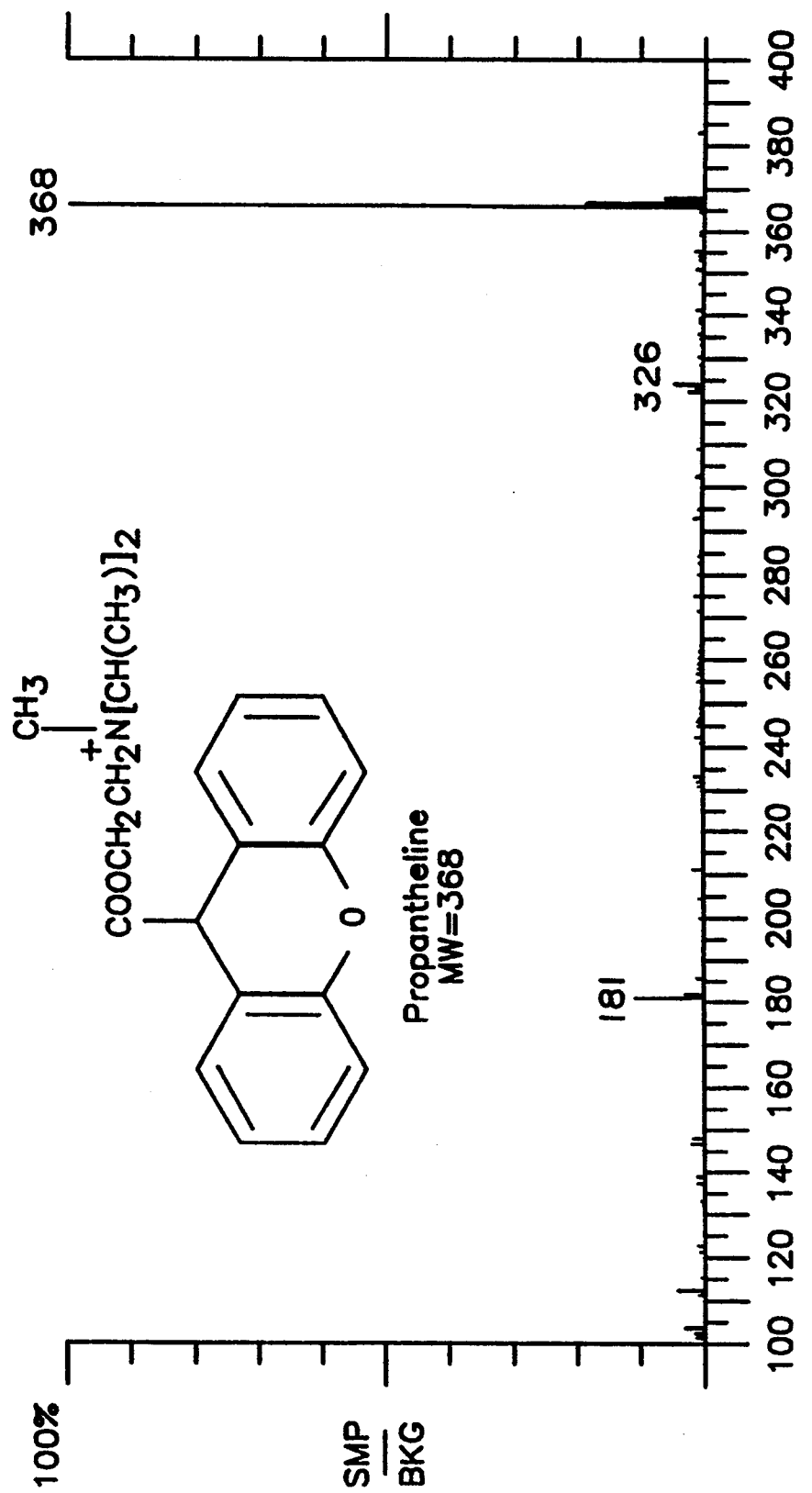
FIG. 17 is a full-scan mass spectrum from 5 ng propantheline from FIG. 16. Peaks at m/z 368, 326 and 181 are suggested to be $M^+$; $(M^+ - C_3H_6)$ and $(C_6H_4CHOC_6H_4)^+$ respectively.

Results of the on-line coupling of HPLC to the ion trap apparatus of FIG. 1 are shown in FIG. 16. A synthetic mixture containing 5 ng of each drug was injected on-column under micro HPLC conditions. The total column effluent (40 µL/min) was directed to the mass spectrometer in this experiment. The potential drop across the first vacuum region was 70 V. Panel A of FIG. 16 is the total ion current with a scan range from 100–400 amu, while panels B-E of FIG. 16 are the extracted ion current profiles of the molecular ions of ipratropium, neostigmine, glycopyrrolate and propantheline, respectively. FIG. 17 shows the full-scan mass spectrum of propantheline (peak at scan #138, FIG. 16) as an example of a typical mass spectrum acquired from 5 ng of drug. The base peak is the molecular ion, m/z=368, while the mild declustering conditions used also lead to the formation of two minor fragment ions at m/z=181 and 326.

Although the invention has been described in terms of a preferred embodiment, it will be apparent that variations and modifications can be made without departing from the true spirit and scope thereof, as set forth in the following claims.

What is claimed is:

1. An atmospheric pressure ion sampling device, comprising:
    a housing having a sampling inlet means;
    means producing an interface vacuum region and an analyzer vacuum region within said housing;
    means adjacent said housing for producing at atmospheric pressure charged particles including ions to be sampled;
    liquid shield means interposed between said sampling inlet means and said means producing charged particles and having an aperture aligned with an orifice in said sampling inlet means;
    means accelerating said charged particles and ions toward said shield means and transporting selected particles and ions through said aperture and said sampling inlet orifice into said interface vacuum region; and
    means transporting said selected ions from said interface vacuum region to said analyzer vacuum region.

2. The device of claim 1, wherein said means for producing charged particles including ions comprises means producing a spray of ionized liquid microdroplets.

3. The device of claim 1, wherein said means for producing charged particles including ions comprises a first capillary connected to a source of analyte liquid;
    a second capillary having an outlet;
    means applying gas under pressure to said second capillary to direct said analyte liquid from said first capillary through said second capillary outlet in a liquid droplet spray; and
    means applying an electric potential to said liquid to produce ions on said droplets.

4. The device of claim 3 wherein said second capillary surrounds said first capillary.

5. The device of claim 1, wherein said interface vacuum region has a pressure of between about 0.01 and about 100 Torr, and wherein said sampling inlet orifice has a diameter sufficient to enable the vacuum in said interface vacuum region to draw ions passing through said shield aperture into said interface vacuum region.

6. The device of claim 1, wherein said liquid shield means includes an electrically conductive plate for preventing excess liquid analyte from reaching said sampling inlet orifice.

7. The device of claim 6, wherein said liquid shield means includes plural spaced, parallel plates having coaxial apertures.

8. The device of claim 1, wherein said liquid shield means is located in a soaking region of said sampling inlet orifice to prevent accidental plugging of said orifice.

9. The device of claim 1, wherein said shield comprises a disk having a central, raised mesa portion in which said aperture is located.

10. The device of claim 1, wherein said liquid shield means is spaced between about 0.1 mm and about 10 mm from said sampling inlet orifice and wherein the diameter of said aperture is between about 0.1 mm and about 10 mm.

11. The device of claim 1, further including heater means between said liquid shield means and said sampling inlet orifice.

12. The device of claim 1, wherein said means accelerating said charged particles comprises a high linear velocity carrier gas.

13. The device of claim 1, wherein said means accelerating said charged particles comprises first electrode means in said housing.

14. The device of claim 13, wherein said means accelerating said charged particles comprises a high linear velocity carrier gas.

15. The device of claim 13, wherein said sampling inlet means comprises a plate and wherein said inlet orifice is a nozzle in said plate, said nozzle defining a Mach disk within said interface vacuum region.

16. The device of claim 15, wherein said first electrode means comprises an electrostatic lens assembly with at least a first electrode within said interface vacuum region between said nozzle and said Mach disk.

17. The device of claim 16, wherein said nozzle has an aspect ratio of about $\frac{1}{3}$.

18. The device of claim 16, wherein said means producing said interface and analyzer vacuum regions comprises divider means in said housing, said divider means including an aperture aligned with said nozzle, and wherein said means transporting said selected ions from said interface vacuum region to said analyzer vacuum region includes second electrode means directing said selected ions through said divider aperture.

19. The device of claim 18, wherein said divider means is a flat metal diaphragm having a thickness smaller than the diameter of said divider aperture.

20. The device of claim 19, wherein said first electrode means includes electrostatic lens means defining an electrostatic drift region.

21. The device of claim 20, further including means applying selected electric potentials to said nozzle, said diaphragm and said electrode means for directing and transporting said ions.

22. The device of claim 21, wherein said means applying selected electric potentials are adjustable in the range of $-300$ V to $+300$ V.

23. The device of claim 22, further including a quadrupole ion trap mass analyzer associated with said analyzer vacuum region of said housing.

24. The device of claim 23, wherein said second electrode means includes electrostatic lens means directing said selected ions into said quadrupole ion trap.

25. The device of claim 23, wherein said second electrode means includes gate means for selectively deflecting said selected ions away from said quadrupole ion trap.

26. The device of claim 1, wherein said means producing said interface and said analyzer vacuum regions comprises a metal diaphragm having a central aperture, and wherein said sampling inlet means comprises a metal capillary tube having a first end adjacent said liquid shield means and having a second end extending into said interface vacuum region, said capillary having a central orifice aligned with said liquid shield and said diaphragm apertures to transport said selected ions to said analyzer vacuum region.

27. The device of claim 26, wherein the aspect ratio of said diaphragm aperture is significantly greater than 1.

28. The device of claim 26, further including means applying selected electrical potentials to said capillary tube and said diaphragm for adjusting the degree of ion fragmentation in said analyzer vacuum region for identification of analyzed ion species.

29. The device of claim 28, further including a quadrupole means analyzer and an electron multiplier associated with said mass analyzer vacuum region.

30. The device of claim 29, wherein said mass analyzer vacuum region includes first and second vacuum chambers, said quadrupole mass analyzer being located in said second vacuum chamber.

31. The device of claim 30, wherein said means transporting said selected ions comprises two spaced-apart, three-electrode lens assemblies located in said first vacuum chamber.

32. The device of claim 29, wherein said mass analyzer vacuum region includes first and second vacuum chambers, said first chamber being adjacent said diaphragm, said quadrupole mass analyzer being located in said first vacuum chamber and an electron multiplier located in said second vacuum chamber and responsive to said mass analyzer.

33. The device of claim 32, further including second diaphragm means between said first and second vacuum chambers, and including a second diaphragm aperture for admitting ions from said mass analyzer to said electron multiplier.

34. The device of claim 33, further including a three-electrode electrostatic ion focusing assembly between said mass analyzer and said second diaphragm aperture.

35. An ion trap sampling device, comprising:
vacuum chamber means;
an inlet sampling nozzle for said vacuum chamber;
an outlet from said vacuum chamber; and
liquid shield means spaced from said inlet nozzle for directing ions at atmospheric pressure from an ion spray source to said sampling nozzle.

36. The device of claim 35, wherein said liquid shield is located in a soaking region of said inlet sampling nozzle to prevent liquid droplets from an ion spray from plugging said nozzle.

37. The device of claim 36, wherein said liquid shield is spaced between about 1 and about 5 mm from said nozzle.

38. The device of claim 37, further including heater means between said nozzle and said input shield.

* * * * *